United States Patent [19]

Misra et al.

[11] Patent Number: 5,371,091

[45] Date of Patent: Dec. 6, 1994

[54] HETEROAROMATIC AMINE THROMBIN INHIBITORS

[75] Inventors: Raj N. Misra, Hopewell; Steven E. Hall, Pennington, both of N.J.

[73] Assignee: Bristol-Myers Squibb Company, Princeton, N.J.

[21] Appl. No.: 76,224

[22] Filed: Jun. 14, 1993

Related U.S. Application Data

[63] Continuation-in-part of Ser. No. 937,271, Aug. 31, 1992, abandoned.

[51] Int. Cl.[5] .............. A61K 31/445; A61K 31/415; A61K 31/42; C07D 215/14

[52] U.S. Cl. .................. 514/314; 514/252; 514/253; 514/255; 514/269; 514/275; 514/318; 514/321; 514/323; 514/326; 544/338; 544/331; 544/332; 544/336; 544/408; 544/409; 546/193; 546/194; 546/198; 546/200; 546/205; 546/209; 546/210; 546/211

[58] Field of Search .............. 546/193, 194, 198, 200, 546/205, 209, 210, 211; 514/314, 318, 321, 323, 326, 252, 253, 269, 275, 255; 544/238, 331, 332, 336, 408, 409

[56] References Cited

U.S. PATENT DOCUMENTS

| | | |
|---|---|---|
| 4,055,651 | 10/1977 | Okamoto et al. |
| 4,066,758 | 1/1978 | Okamoto et al. |
| 4,066,773 | 1/1978 | Okamoto et al. |
| 4,069,323 | 1/1978 | Okamoto et al. |
| 4,073,914 | 2/1978 | Kikumoto et al. |
| 4,117,127 | 9/1978 | Okamoto et al. |
| 4,201,863 | 5/1980 | Okamoto et al. |
| 4,258,192 | 3/1981 | Okamoto et al. |
| 4,764,618 | 8/1988 | Kikumoto et al. |
| 5,141,947 | 8/1992 | Tamao et al. ............ 514/314 |

OTHER PUBLICATIONS

Angliker, Herbert et al, "Pseudoarginine: synthesis and properties of derivatives of δ-(1-imidazolyl) norvaline" Biochem. J. (1990) 266, 829–834.

Hijikata-Okunomiya, Akiko et al, "A Strategy for a Rational Approach to Designing Synthetic Selective Inhibitors" Seminars in Thrombosis and Hemostasis-vol. 18, No. 1, 1992.

*Primary Examiner*—Johann Richter
*Assistant Examiner*—John Peabody
*Attorney, Agent, or Firm*—Burton Rodney

[57] ABSTRACT

Sulfonamide thrombin inhibitors are provided which have the structure

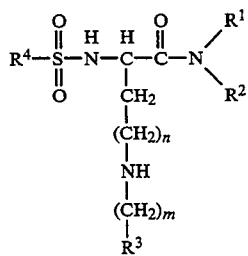

including all stereoisomers thereof, wherein n is 1, 2 or 3; m is 0, 1 or 2; $R^1$ and $R^2$ are independently H, lower alkyl, cycloalkyl, aryl, heteroaryl or heteroaryl-alkyl, or $R^1$ and $R^2$ can be taken together with the N atom to which they are attached to form a 4- to 8-membered ring; $R^3$ is monocyclic heteroaryl; and $R^4$ is alkyl, cycloalkyl, aryl, heteroaryl, quinolinyl or tetrahydroquinolinyl, and pharmaceutically acceptable salts thereof.

17 Claims, No Drawings

HETEROAROMATIC AMINE THROMBIN INHIBITORS

REFERENCE TO OTHER APPLICATIONS

This is a continuation-in-part of U.S. application Ser. No. 937,271 filed Aug. 31, 1992, now abandoned.

FIELD OF THE INVENTION

The present invention relates to heretoaromatic amines, which are thrombin inhibitors and thus inhibit formation of thrombi.

DESCRIPTION OF THE INVENTION

In accordance with the present invention compounds are provided which are thrombin inhibitors which have the structure I

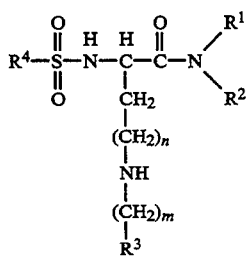

including all stereoisomers thereof, wherein n is 1, 2 or 3;

m is 0, 1 or 2;

$R^1$ and $R^2$ may be the same or different and are independently hydrogen, lower alkyl, cycloalkyl, aryl, heteroaryl, or heteroarylalkyl, or $R^1$ and $R^2$ can be taken together with the nitrogen atom to which they are attached to form a 4- to 8- membered N-containing heterocyclic ring which may be unsubstituted or substituted on a carbon atom with lower alkyl, carboxy, carboalkoxy, aryl or cycloalkyl, or any of lower alkyl, aryl or cycloalkyl linked through an O, S or N atom to the heterocyclic ring.

In addition, the 4- to 8- membered N-containing heterocyclic ring may contain an additional N, O or S.

$R^3$ is monocyclic heteroaryl; and $R^4$ is alkyl, cycloalkyl, aryl, tetrahydronaphthyl, heteroaryl, quinolinyl, or tetrahydroquinolinyl; and pharmaceutically acceptable salts thereof.

The term "lower alkyl" or "alkyl" as employed herein by itself or as part of another group includes both straight and branched chain radicals of up to 18 carbons, preferably 1 to 8 carbons, such as methyl, ethyl, propyl, isopropyl, butyl, t-butyl, isobutyl, pentyl, hexyl, isohexyl, heptyl, octyl, 2,2,4- trimethylpentyl, nonyl, decyl, undecyl, dodecyl, the various branched chain isomers thereof, and the like as well as such groups including 1, 2 or 3 halo substituents, an aryl substituent, an alkylaryl substituent, a haloaryl substituent, a cycloalkyl substituent, an alkylcycloalkyl substituent, an alkenyl substituent, an alkynyl substituent, hydroxy and/or a carboxy substituent.

The term "cycloalkyl" by itself or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with substituents such as halogen, lower alkyl, alkoxy and/or hydroxy group.

The term "aryl" or "Ar" as employed herein by itself or as part of another group refers to monocyclic or bicyclic aromatic groups containing from 6 to 10 carbons in the ring portion, such as phenyl, naphthyl, or tetrahydronaphthyl, Aryl(or At), phenyl, naphthyl may include substituted aryl, substituted phenyl or substituted naphthyl, which may include 1 or 2 substituents on either the phenyl or naphthyl such as lower alkyl, cyano, amino, alkylamino, dialkylamino, nitro, carboxy, carboalkoxy, trifluoromethyl, halogen (Cl, Br, I or F), lower alkoxy, arylalkoxy, hydroxy, alkylthio, alkylsulfinyl, alkylsulfonyl, arylthio, arylsulfinyl and/or arylsulfonyl.

The term "aralkyl", "aryl-alkyl" or "aryl-lower alkyl" as used herein by itself or as part of another group refers to lower alkyl groups as discussed above having an aryl substituent, such as benzyl.

The term "lower alkoxy", "alkoxy" or "aralkoxy" includes any of the above lower alkyl, alkyl or aralkyl groups linked to an oxygen atom.

The term "halogen" or "halo" as used herein by itself or as part of another group refers to chlorine, bromine, fluorine or iodine with chlorine being preferred.

The term "lower alkenyl" or "alkenyl" by itself or as part of another group as employed herein includes a carbon chain by itself or as part of another group of up to 16 carbons, preferably 3 to 10 carbons, containing one double bond such as propenyl, 2-butenyl, 3-butenyl, 2-pentenyl, 4-pentenyl and the like, and may include a halogen substituent such as I, Cl, or F.

The term "lower alkenyl" or "alkynyl" by itself or as part of another group as employed herein includes a carbon chain of up to 16 carbons, preferably 3 to 10 carbons, containing one triple bond such as 2-propynyl, 2-butynyl, 3-butynyl and the like.

The term "monocyclic heteroaryl" or "heteroaromatic" used in reference to $R^3$, refers to a 5- to 6-membered monocyclic aromatic ring which includes at least one nitrogen atom and optionally 1 or 2 hetero atoms such as nitrogen, oxygen or sulfur, for example,

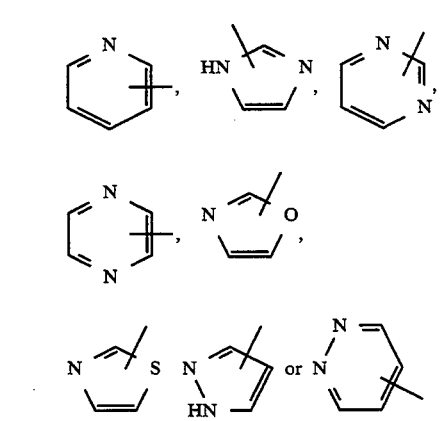

The term "heteroaryl" by itself or as part of another group used in reference to $R^4$ refers to a 5- to 10-membered monocyclic or bicyclic aromatic ring which includes at least one nitrogen or oxygen atom and optionally 1 to 3 hereto atoms such as nitrogen, oxygen or sulfur, such as any of the monocyclic heteroaryl groups set out above as well as

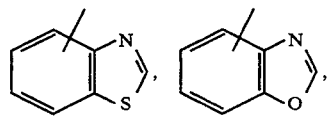

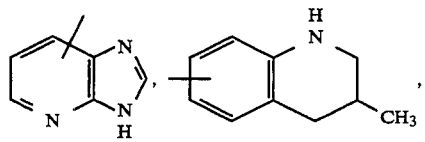

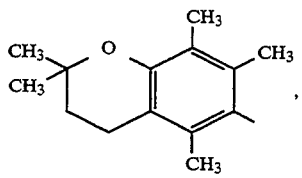

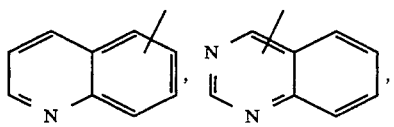

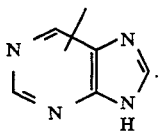

The heteroaryl rings and monocyclic heteroaryl or heteroaromatic rings may optionally include 1 or 2 substituents such as halogen (Cl, Br, F or CF$_3$), lower alkyl, lower alkoxy, carboxy, amino, lower alkylamino and/or di-lower alkylamino.

Preferred are compounds of formula I wherein $R^4$ is aryl, preferably 2-naphthyl, tetrahydroquinoline or 7-alkoxy-2-naphthyl, such as 7-methoxy-2-naphthyl

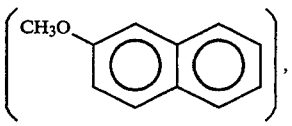

most preferably 7-methoxy-2-naphthyl, n is 2, m is 0, $R^3$ is 2-pyridinyl, and $R^1$ and $R^2$ are taken together to form a 5 to 7 membered heterocyclic ring which preferably is piperidinyl such as alkyl-substituted piperidinyl, most preferably 4-methyl piperidinyl or 2-carboxy-4-methyl-piperidinyl.

Preferred are compounds of the invention having the structure IA in which the stereochemistry of the α-carbon is S.

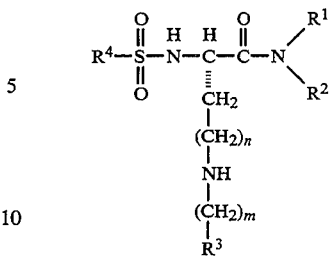

The compounds of formula I of the invention may be prepared as outlined below.

Compounds of formula I wherein n is 2 or 3 may be prepared starting with alcohol II

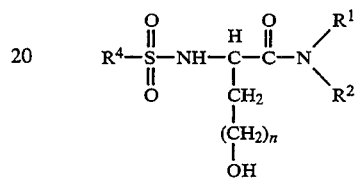

(preferably where stereochemistry on α carbon is S) which is subjected to an oxidation reaction, for example a Dess-Martin oxidation wherein a solution of alcohol II in an inert organic solvent such as methylene chloride or chloroform, is treated with Dess-Martin periodinane (prepared as described in Dess, D.B.; Martin, J.C.; J. Org. Chem., 1983, 48, 4155) followed by pyridine to form aminal III

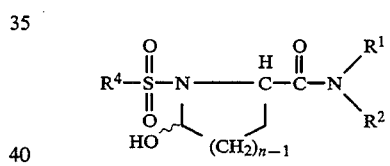

Aminal III is then made to undergo imine formation by treating III with an amine IV $$H_2N-(CH_2)_m-R^3 \qquad (IV)$$

in toluene, benzene or xylene, optionally in the presence of an acid catalyst such as camphorsulfonic acid, at from about 25° to about 140° to form imine V

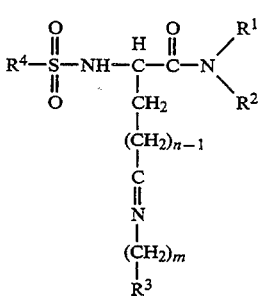

Imine V is then reduced by treating V with a reducing agent such as lithium borohydride, sodium borohydride or sodium cyanoborohydride optionally in the presence of a catalyst such as acetic acid, and the like to form the formula I compound of the invention wherein n is 2 or 3, that is IB

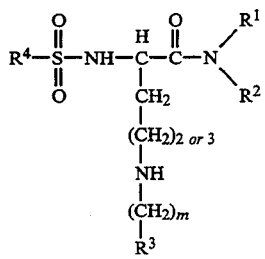

IB

Compounds of formula I wherein n is 1, may be prepared starting with alcohol II (where n=1) which is made to undergo iodide formation by treating a solution of alcohol II in dry acetonitrile, with N,N'-carbonyldiimidazole and then with iodomethane to form iodide VI

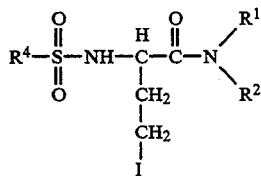

VI

Iodide VI is then treated with a solution of the sodium anion of amine IV in dry inert organic solvent such as dry tetrahydrofuran, under an inert atmosphere such as argon, to form the formula I compound of the invention wherein n is 1, that is IC

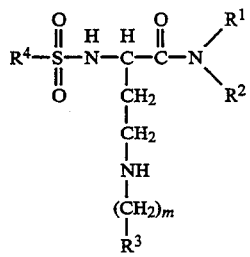

IC

In an alternative procedure, compounds of the invention I where n is 1, 2 or 3 may be prepared starting with amine XII

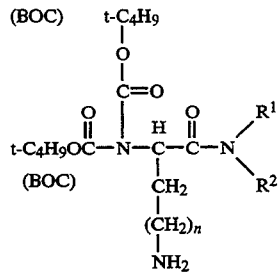

XII (preferably where stereochemistry on α carbon is S) which is treated with a halogenated heteroaryl XIII where X=Br, Cl, I

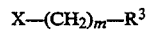 (XIII)

in the presence of anhydrous alcohol, such as methanol, ethanol, propanol or butanol, and a weak base such as sodium bicarbonate or triethylamine, at an elevated temperature of within the range of from about 55° to about 150° C., depending upon the alcohol solvent employed, to form protected compound XIV

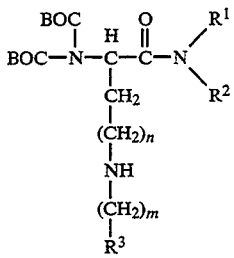

XIV which is made to undergo a deprotecting reaction wherein XIV is treated with hydrogen chloride in the presence of dioxane or trifluoroacetic acid in dichloromethane to form XV

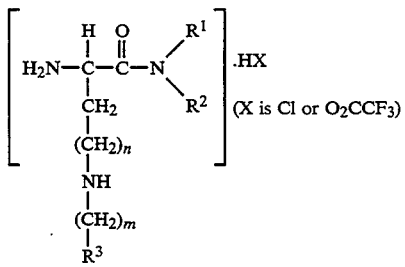

XV

Amine salt XV is then treated with a sulfonyl chloride XVI $$R^4-SO_2-Cl \qquad (XVI)$$

in the presence of an organic base such as triethylamine or diisopropylethylamine, and an inert organic solvent such as dichloromethane, chloroform or THF, under an inert atmosphere such as argon at a reduced temperature of from about −20° to about 15° C., to form the sulfonamide I of the invention.

The amine XII may be prepared starting with alcohol IIA where n is 1, 2 or 3, according to the following reaction sequence.

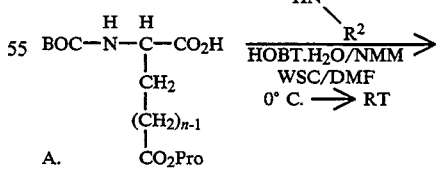

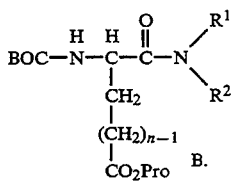

B.

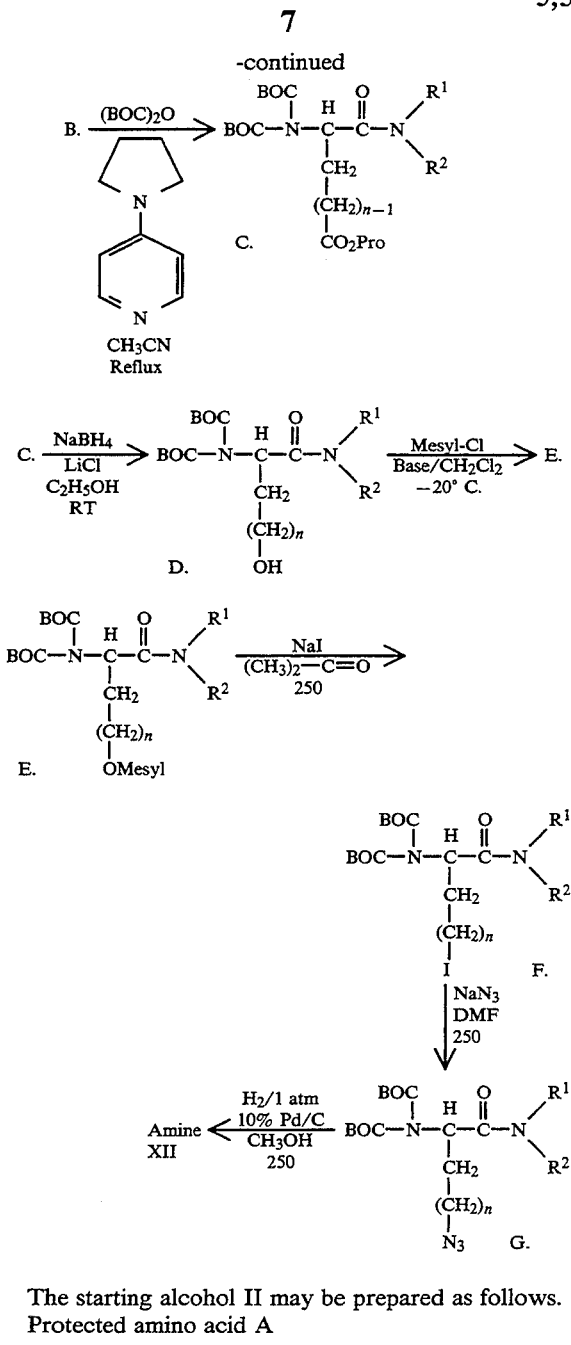

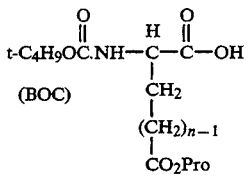

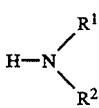

The starting alcohol II may be prepared as follows. Protected amino acid A wherein Pro is methyl, ethyl or benzyl, is made to undergo a carbodiimide coupling reaction with amine XVIII in the presence of ethyl 3-(3-dimethylamino)propylcarbodiimide hydrochloride (WSC) or dicyclohexylcarbodiimide (DCC), and 1-hydroxybenzotriazole monohydrate (HOBT), and N-methylmorpholine (NMM) or triethylamine, and an inert organic solvent such as dimethylformamide (DMF), or tetrahydrofuran (THF), under an inert atmosphere such as argon, to form amide B.

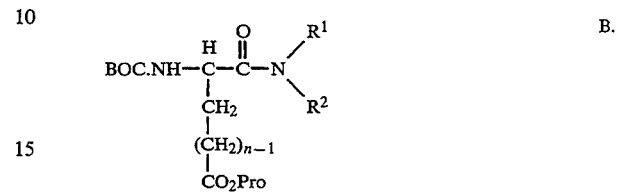

Amide XIX is made to undergo a deprotecting reaction wherein amide XIX is treated with trifluoroacetic acid in dichloromethane or hydrogen chloride in dioxane, under an inert atmosphere such as argon, at reduced temperature of from about 0° to about 25° C., to form amide XX

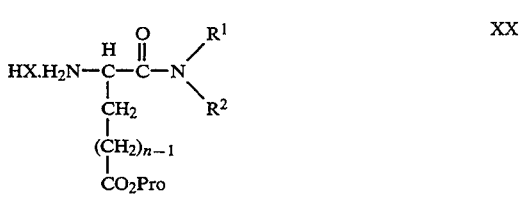

Amide XX is then made to undergo sulfonamide formation by treating XX in the presence of an inert organic solvent such as dichloromethane, chloroform or tetrahydrofuran, under an inert atmosphere such as argon at a reduced temperature of from about −20° to about 15° C., with a sulfonyl chloride of the structure XVI

and organic base such as triethylamine or diisopropylethylamine, to form sulfonamide XXII

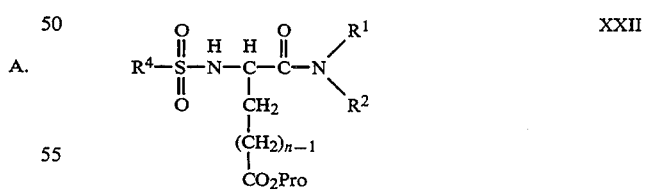

Sulfonamide XXII is then reduced by treatment with diisobutylaluminum hydride (DIBAL-H) in the presence of an inert organic solvent such as THF or methylene chloride or toluene or with sodium borohydride, in the presence of lithium chloride and ethanol, under an inert atmosphere such as argon to form alcohol II.

The compounds of formula I of the invention can be obtained as pharmaceutically acceptable acid addition salts by reacting a free base with an acid, such as hydrochloric, hydrobromic, hydroiodic, nitric, sulfuric, phosphoric, acetic, citric, maleic, succinic, lactic, tartaric, gluconic, benzoic, methanesulfonic, ethanesulfonic, benzenesulfonic, p-toluenesulfonic acid or the like. In a similar manner, the product can be obtained as pharmaceutically acceptable salts by reacting a free carboxylic acid with a base, such as sodium hydroxide, potassium hydroxide, ammonium hydroxide, triethylamine, procaine, dibenzylamine, 1-ephenamine, N,N'-dibenzylethylenediamine, N-ethylpiperidine, arginine, lysine or the like.

The compounds of the present invention are serine protease inhibitors, and in particular inhibit thrombin, Factor Xa, and/or trypsin. The compounds of the present invention are useful for the treatment or prophylaxis of those processes which involve the production and/or action of thrombin. This includes a number of thrombotic and prothrombotic states in which the coagulation cascade is activated which include, but are not limited to, deep vein thrombosis (DVT), consumptive hemorrhagic disorders (such as disseminated intravascular coagulopathy (DIC), renal allograft rejection and hemolytic uremic syndrome) Kasabach-Merritt syndrome, pulmonary embolism, myocardial infarction, stroke, thromboembolic complications of surgery (such as coronary artery bypass graft, hip replacement and endarterectomy) and peripheral arterial occlusion. In addition to its effects on the coagulation process, thrombin has been shown to activate a large number of cells (such as neutrophils, fibroblasts, endothelial cells, and smooth muscle cells). Therefore, the compounds of the present invention may also be useful for the treatment or prophylaxis of adult respiratory distress syndrome, septic shock, septicemia, inflammatory responses which include, but are not limited to, edema, acute or chronic atherosclerosis, and reperfusion damage.

The compounds of the invention may also be useful in treating neoplasia/metastasis (in particular those which utilize fibrin) and neurodegenerative diseases such as Alzheimer's disease and Parkinson's disease. In addition, the compounds of the present invention may be useful to prevent restenosis following arterial injury induced by endogenous (rupture of an atherosclerotic plaque) or exogenous (invasive cardiological procedure) events.

The compounds of the present invention may also be used as an anticoagulant in extracorporeal blood circuits, such as those necessary in dialysis and surgery (such as coronary artery bypass surgery).

The compounds of the present invention may also be used in combination with thrombolyic agents, such as tissue plasminogen activator (natural or recombinant), streptokinase, urokinase, prourokinase, anisolated streptokinase plasminogen activator complex (ASPAC), animal salivary gland plasminogen activators, and the like. The compounds of the present invention may act in a synergistic fashion to prevent reocclusion following a successful thrombolytic therapy and/or reduce the time to reperfusion. The compounds of the present invention may also allow for reduced doses of the thrombolytic agent to be used and therefore minimize potential hemmorhagic side-effects. The compounds of the present invention may also prevent acute long-term reocclusion and/or restenosis following arterial recanalization procedures, including, but not limited to, balloon angioplasty, placement of arterial stents, and laser and/or mechanical atherectomy procedures.

The compounds of the present invention may also be used in combination with other antithrombotic or anticoagulant drugs such as thromboxane receptor antagonists, prostacyclin mimetics, phosphodiesterase inhibitors, fibrinogen antagonists, and the like.

Compounds of the present invention that inhibit trypsin may also be useful for the treatment of pancreatitis.

The compounds of the invention can be administered orally or parenterally to various mammalian species known to be subject to such maladies, e.g., humans, cats, dogs and the like in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) on a regimen in single or 2 to 4 divided daily doses, for a period necessary to alleviate the condition requiring treatment in accordance with the invention.

The active substance can be utilized in a composition such as tablet, capsule, solution or suspension containing about 5 to about 500 mg per unit of dosage of a compound or mixture of compounds of formula I. The compounds of the invention may be compounded in conventional manner with a physiologically acceptable vehicle or carrier, excipient, binder, preservative, stabilizer, flavor, etc., as called for by accepted pharmaceutical practice.

The following Examples represent preferred embodiments of the present invention. Unless otherwise indicated, all temperatures are expressed in degrees Centigrade.

EXAMPLE 1

(S)—N—[1—[(4-Methyl-1-piperidinyl)carbonyl]—4-(4-pyridinylamino)butyl]-2-naphthalenesulfonamide A. (S)-β-[[(1,1-Dimethylethoxy)carbonyl]-amino]-4-methyl-α-oxo-1-piperidinepentanoic acid, phenylmethyl ester To a stirred mixture of N-Boc-L-glutamic acid-β-benzyl ester (3.00 g, 8.90 mmol) and 1-hydroxybenzotriazole monohydrate (HOBT) (1.50 g, 8.90 mmol) in 40 mL of DMF under argon was added in order N-methylmorpholine (1.96 mL, 17.8 mmol), 4-methylpiperidine (1.05 mL, 8.90 mmol) and ethyl-3-(3-dimethylamino)-propylcarbodiimide hydrochloride (WSC) (1.71 g, 8.90 mmol). The mixture was stirred at room temperature for 15 hours and concentrated in vacuo. The resulting crude oil was dissolved in 300 mL of ethyl acetate (EtOAc) and washed with 0.2 N aqueous NaOH (2×60 mL), 1N aqueous HCl (2×60 mL), saturated NaHCO$_3$ solution (1×60 mL) and brine (1×60 mL). The EtOAc layer was dried over MgSO$_4$, filtered and concentrated in vacuo to give title amide (3.63 g, 98%).

B. (S)-β-Amino-4-methyl-α-oxo-1-piperidinepentanoic acid, phenylmethyl ester, hydrochloride To a stirred mixture of Part A amide (3.43 g, 8.21 mmol) in 20 mL of dry dichloromethane under argon at 0° was added 40 mL of trifluoroacetic acid (TFA). The mixture was stirred at 0° C. for 1.5 h and at room temperature for 2 h. The mixture was diluted with 100 mL of toluene and concentrated in vacuo. The residue was treated with 30 mL of 4N HCl in ether, diluted with 100 mL of toluene and concentrated in vacuo to give title amine hydrochloride in a quantitative yield.

C. (S)-4-Methyl-β-[(2-naphthalenylsulfonyl)-amino]-α-oxo-1-piperidinepentanoic acid, phenylmethyl ester To a stirred mixture of Part B amine hydrochloride in 120 mL of dry dichloromethane under argon at 0° was added in order 2-naphthalenesulfonyl chloride (1.73 g 7.62 mmol) and triethylamine (3.18 mL, 22.8 mmol).

The mixture was stirred at 0° for 1 hour, diluted with 600 mL of EtOAc and washed with 1N aqueous HCl (3×100 mL), saturated NaHCO₃ solution (2×100 mL) and brine (1×100 mL). The organic layer was dried over MgSO₄, filtered and concentrated in vacuo. This was chromatographed on 150 g of Merck 60 silica gel using 1% CH₃OH/CH₂Cl₂ as eluant to give 2.80 g (72%) of title sulfonamide.

D. (S)-N-[4-Hydroxy-1-[(4-methyl-1-piperidinyl)carbonyl]butyl]-2-naphthalenesulfonamide To a stirred mixture of Part C sulfonamide (1.44 g, 2.83 mmol) in 72 mL of dry THF under argon at −78° C. was added 1M DIBAL-H in hexane (14.2 mL, 14.2 mmol) dropwise over 20 minutes. The mixture was slowly warmed to −45° over 3.5 hours and the temperature was kept at −45° for 1 hour. The mixture was cooled to −78° and quenched slowly with addition of 10 mL of acetone. The mixture was then cooled in an ice bath and combined slowly with 33 g of a mixture of 9:1 silica gel-water. To this vigorously stirred mixture was added 2.9 mL of water. The mixture was stirred at 0° for 30 minutes and filtered. The silica gel cake was rinsed with acetone (3×30 mL). The filtrate was concentrated in vacuo. Purification was effected by a flash chromatography on 55 g of Merck silica gel 60 using 3% CH₃OH/CH₂Cl₂ as eluant to give 0.81 g (71%) of title alcohol.

E. (2S)-(4-Methyl-1-piperidinyl) [5-hydroxy-1-(2-naphthalenylsulfonyl)-2-pyrrolidinyl]-methanone To a solution of 1.00 g (2.47 mmol) of Part D alcohol in 50 mL of dry CH₂Cl₂ (distilled from P₂O₅), stirred at room temperature, was added in several portions 2.94 g (4.47 mmol, prepared via procedure of: Dess, D. B.; Martin, J. C.; *J Org Chem*, 1983, 48, 4155.) of Dess Martin periodinane, followed by 400 μL (4.94 mmol, Baxter, purified by passing through basic alumina) of pyridine. The reaction was stirred at room temperature for 1 hour, then 150 mL of ether, followed by 150 mL saturated NaHCO₃ solution containing 5.5 g sodium thiosulfate were added. The mixture was stirred until the organic layer was clear. The organic layer was separated, washed with 150 mL of saturated NaHCO₃ solution, 150 mL of brine, dried (MgSO₄) and concentrated in vacuo to give a white foam. The crude foam was flash chromatographed (Merck silica, 50×150 mm, 1% methanol/methylene chloride) to give 730 mg (1.81 mmol, 73%) of title compound as a white foam. The 270 MHz ¹H NMR (CDCl₃) of title compound indicated it was a mixture of aminal and aldehyde (predominantly aminal).

F. (S)-N-[1-[(4-Methyl-1-piperidinyl)carbonyl]-4-(4-pyridinylimino)butyl]-2-naphthalenesulfonamide A solution of 210 mg (0.523 mmol) of Part E compound, 49 mg (0.52 mmol, Aldrich) of 4-aminopyridine and 5 mg (0.02 mmol, Aldrich) of (1R)-(−)-10-camphorsulfonic acid in 10 mL of toluene (Burdick & Jackson) was refluxed, with a Dean Stark setup, for 72 h. The reaction was then cooled to room temperature, and concentrated in vacuo to give a crude orange oil. The crude oil was flash chromatographed (Merck silica, 25×75 mm, 1:9 methanol/methylene chloride) to give 163 mg (0.341 mmol, 65%) of title imine as a white foam.

G. (S)-N-[1-[(4-Methyl-1-piperidinyl)-carbonyl]-4-(4-pyridinylamino)butyl]-2-naphthalenesulfonamide To a solution of 160 mg (0.334 mmol) of Part F imine in 6 mL of dry THF (distilled from K/Ph₂CO), stirred at room temperature, was added 10 mg (0.44 mmol, Aldrich) of lithium borohydride. The reaction was stirred at room temperature for 1 h, then quenched by the dropwise addition of 0.5 mL of methanol, followed by 1 mL of water. The reaction mixture was concentrated in vacuo to give a white solid. The white solid was partitioned between 20 mL ethyl acetate/20 mL water; the water layer was separated and extracted with 3–10 mL portions of ethyl acetate. The combined organic layers were washed with 20 mL brine, dried (Na₂SO₄), azeotroped three times with 20 mL methanol and concentrated in vacuo to give a white foam. The crude foam was flash chromatographed (Merck silica, 5×20 mm, 1:9 (Jan. 10, 1989 ammonium hydroxide/methanol/methylene chloride)/methylene chloride) to give 154 mg (0.320 mmol, 96%) of title amine as a white foam.

Analysis Calc'd:C₂₆H₃₂N₄O₃S+1.13 mol H₂O: C, 62.34; H, 6.89; N, 11.18; S, 6.40

Found: C, 62.57; H, 7.11; N, 10.95; S, 6.64

EXAMPLE 2

(S)-N-[1-[(4-Methyl-1-piperidinyl)carbonyl]-4-(2-pyridinylamino)butyl]-2-naphthalenesulfonamide A. (S)-N-[1-[(4-Methyl-1-piperidinyl)carbonyl]-4-(2-pyridinylimino)butyl]-2-naphthalenesulfonamide A solution of 347 mg (0.862 mmol), of Example 1 Part E compound and 81 mg (0.86 mmol, Aldrich) of 2-aminopyridine in 50 mL of toluene (Burdick & Jackson) was refluxed, with a Dean Stark setup, for 48 h. Then an additional portion of 8 mg (0.17 mmol) of 2-aminopyridine was added; after 16 h, 40 mg (0.43 mmol) of 2-aminopyridine was added. The reaction was refluxed for an additional 5 h, then cooled to room temperature and concentrated in vacuo to give a crude orange oil. Thee crude oil was flash chromatographed (Merck silica, 50×200 mm, 3:2 ethyl acetate/hexane) to give 320 mg (0.67 mmol, 77%) of title imine as a white foam.

B. (S)-N-[1-[(4-Methyl-1-piperidinyl)carbonyl]-4-(2-pyridinylamino)butyl]-2-naphthalenesulfonamide To a solution of 300 mg (0.627 mmol) of Part A imine in 12 mL of dry THF (distilled from K/Ph₂CO), stirred at zoom temperature, was added 18 mg (0.81 mmol, Aldrich) of lithium borohydride. The reaction was stirred at room temperature for 1 h, then quenched by the dropwise addition of 1 mL of methanol, followed by 2 mL of water. The reaction mixture was concentrated in vacuo to give a white solid. The white solid was partitioned between 100 mL CH₂Cl₂/H₂O; the water layer was separated and extracted with 2–50 mL portions of methylene chloride. The combined organic layers were dried (Na₂SO₄) and concentrated in vacuo to give a white solid. To a solution of the crude white solid in 20 mL sieve-dried methanol (Burdick & Jackson), stirred at 0°, was added dropwise a solution of acidic methanol (prepared by the addition of 1 mL acetyl chloride to 10 mL methanol). The reaction mixture was stirred at room temperature for 30 minutes, then partitioned between 100 mL CH₂Cl₂/100 mL saturated NaHCO₃ solution. The organic layer was separated, washed with brine, dried (Na₂SO₄) and concentrated in vacuo to give a clear oil. The crude oil was flash chromatographed (Merck silica, 50×200 mm, 3:97 methanol/methylene chloride) to give crude white solid, which was recrystallized from hot ethyl acetate/hexane to give 160 mg (0.332 mmol, 53%) of title amine as a white solid, mp 135°–137°.

Analysis Calc'd for C₂₆H₃₂N₄O₃S: C, 64.98; H, 6.71; N, 11.66; S, 6.67

Found: C, 64.92; H, 6.61; N, 11.58; S, 6.40

EXAMPLE 3

(S)-N-[1-[(4-Methyl-1-piperidinyl)carbonyl]-3-(2-pyridinylamino)propyl]-2-naphthalenesulfonamide, trifluoroacetic acid salt A. (S)-β-[[(1,1-Dimethylethoxy)carbonylamino]-4-methyl-α-oxo-1-piperidinebutanoic acid phenylmethyl ester To a solution of 12.5 g (38.65 mmol, Bachem) of N-Boc-L-aspartic acid-β-benzyl ester in 75 mL of sieve-dried DMF (Burdick & Jackson), cooled to 0°, was added 5.04 mL (42.5 mmol, Aldrich) of 4-methylpiperidine, 6.51 g (42.5 mmol, 80%, Aldrich & Schweizerhall) of HOBT hydrate and 4.70 mL (42.5 mmol, Aldrich) of N-methylmorpholine. The reaction was stirred at 0° for 10 minutes, then 8.15 g (42.5 mmol, JBL) of WSC was added. The reaction was stirred at 0° for 1 h, then warmed to room temperature and stirred for 16 h. The reaction mixture was concentrated in vacuo and the residue was partitioned between 200 mL of EtOAc/200 mL of 1M HCl; the aqueous Layer was extracted with 2–100 mL portions of EtOAc. The combined EtOAc layers were washed with 100 mL of 1M HCl, 100 mL of saturated NaHCO$_3$ solution, dried (MgSO$_4$) and concentrated in vacuo to give an orange oil. The crude oil was flash chromatographed (Merck silica, 100×200 mm, 1:2 ethyl acetate/hexane) to give 15.33 g (37.94 mmol, 98%) of title amide as a white solid, mp 88°–90°.

B. (S)-β-Amino-4-methyl-α-oxo-1-piperidinebutanoic acid, phenylmethyl ester, hydrochloride To a solution of 15.33 g (37.94 mmol), of Part A amide in 100 mL of 1,4-dioxane (Burdick & Jackson), cooled to 0°, was added dropwise over 45 minutes 50 mL (200 mmol, 4M in dioxane, Aldrich) of HCl solution. The reaction mixture was warmed to room temperature and stirred for 16 h, then sparged with argon for 20 minutes and concentrated in vacuo to give an orange oil. The oil was azeotroped three times with 50 mL of ether, then triturated with 200 mL ether for three hours to form a white solid. The mixture was cooled to 0°; the solid was filtered off and dried in vacuo to give 11.13 g (32.73 mmol, 86%) of title amine hydrochloride as a white solid, mp 126°–129°.

C. (S)-4-Methyl-β-[(2-naphthalenylsulfonyl)amino]-α-oxo-1-piperidinebutanoic acid, phenylmethyl ester To a solution of 7.41 g (32.7 mmol, Aldrich) of 2-naphthalenesulfonyl chloride in 100 mL of dry CH$_2$Cl$_2$ (distilled from P$_2$O$_5$), cooled to 0°, was added 11.40 mL (81.8 mmol, distilled from CaH$_2$) of triethylamine, followed by the dropwise addition of a solution of 11.12 g (32.71 mmol), of Part B amine hydrochloride in 75 mL dry CH$_2$Cl$_2$ over 35 minutes. After stirring at 0° for 3.5 h, the reaction was washed with 2–150 mL portions of 1M HCl, 150 mL of saturated NaHCO$_3$ solution, dried (MgSO$_4$) and concentrated in vacuo to give an oil. The crude oil was flash chromatographed (Merck silica, 100×200 mm, 1:2 ethyl acetate/hexane) to give 13.6 g (27.49 mmol, 84%) of title sulfonamide as a white foam.

D. (S)-N-[3-Hydroxy-1-[(4-methyl-1-piperidinyl)carbonyl]propyl]-2-naphthalenesulfonamide To a solution of 6.81 g (13.77 mmol), of Part C sulfonamide in 140 mL of anhydrous ethanol, stirred at room temperature, was added in one portion 2.34 g (55.1 mmol, Aldrich) of lithium chloride, followed by the portionwise addition of 1.04 g (27.5 mmol, Aldrich) of sodium borohydride. After stirring at room temperature for 4 h, a second portion of 2.34 g (55.1 mmol) of lithium chloride and 1.04 g (27.5 mmol) of sodium borohydride was added. After stirring at room temperature for 16 h, a third portion of 2.34 g (55.1 mmol) of lithium chloride and 1.04 g (27.5 mmol) of sodium borohydride was added. The reaction was stirred at room temperature for 16 h and refrigerated for 3 days. The mixture was quenched at 0° by the dropwise addition of 50 mL of H$_2$O and 50 mL of glacial acetic acid and concentrated in vacuo. The resulting residue was partitioned between 500 mL ethyl acetate/400 mL 1M HCl; the water layer was separated and extracted with 2–200 mL portions of ethyl acetate. The combined ethyl acetate layers were washed with 4–200 mL portions of 1M NaOH, 200 mL brine, dried (MgSO$_4$) and concentrated in vacuo to give a crude oil. The oil was flash chromatographed (Merck silica, 100×200 mm, 4:1 ethyl acetate/hexane) to give 3.05 g (7.81 mmol, 57%) of title alcohol as a white solid, mp 138°–140°.

E. (S)-N-[3-Iodo-1-[(4-methyl-1-piperidinyl)carbonyl]propyl]-2-naphthalenesulfonamide To a solution of 1.75 g (4.48 mmol), of Part D alcohol in 20 mL of dry acetonitrile (Burdick & Jackson), stirred at room temperature, was added 944 mg (5.82 mmol, Aldrich) of N,N'-carbonyldiimidazole. The mixture was stirred at room temperature for 1 h, then 1.39 mL (22 mmol, EM Science) of iodomethane was added dropwise over 10 minutes. The reaction was stirred at room temperature for 16 h and refluxed for 2 h. The reaction mixture was cooled to room temperature and partitioned between 100 mL ethyl acetate/100 mL water. The organic layer was separated, washed with 100 mL 1M HCl, 100 mL saturated NaHCO$_3$ solution, 2–100 mL portions of aqueous Na$_2$S$_2$O$_3$, 100 mL water and 100 mL brine, dried (MgSO$_4$) and concentrated in vacuo to give a red liquid. The crude liquid was flash chromatographed (Merck silica, 50×150 mm, 1:1 ethyl acetate/hexane) to give 910 mg (1.82 mmol, 41%) of title iodide as a white foam.

F. (S)-N-[1-[(4-Methyl-1-piperidinyl)carbonyl]-3-(2-pyridinylamino)propyl]-2-naphthalenesulfonamide To a solution of 253 mg (2.68 mmol, Aldrich) of 2-aminopyridine in 5 mL of dry THF (distilled from K, Ph$_2$CO), stirred at room temperature, was added to 107 mg (60% in oil, 2.68 mmol, Aldrich) of sodium hydride dispersion. After stirring 2 h at room temperature, the solution was added to 384 mg (0.77 mmol) of Part E iodide under argon. The reaction was stirred for an additional hour, then quenched by the dropwise addition of 1 mL of water and concentrated in vacuo. The residue was partitioned between 15 mL CH$_2$Cl$_2$/15 mL water; the water layer was separated and extracted with 2–20 mL portions of CH$_2$Cl$_2$. The combined CH$_2$Cl$_2$ layers were dried (MgSO$_4$) and concentrated in vacuo to give an orange oil. The crude oil was flash chromatographed (Merck silica, 15×180 mm, 1:1 ethyl acetate/hexane) to give an impure oil, which was rechromatographed (Merck silica, 15×180 mm, 1:2 ethyl acetate/hexane) to give an oil with two impurities. A 273 mg portion of the oil was purified by HPLC (YMC, C-18, S-15 ODS, 50×500 mm, 120A, 217 nM, 10:90 CH$_3$CN/H$_2$O to 80:20 CH$_3$CN/H$_2$O over 45 minutes at 90 mL/min) to give 161 mg (0.34 mmol, 45%) of title amine salt as a white foam.

Analysis Calc'd for C$_{25}$H$_{30}$N$_4$O$_3$S+CF$_2$CO$_2$H+0.67 mol H$_2$O: C, 54.72; H, 5.50; N, 9.45; F, 9.62; S, 5.52

Found: C, 54.88; H, 5.29; N, 9.29; F, 9.98; S, 5.60

EXAMPLE 4

(S)-N-[1-[(4-Methyl-1-piperidinyl)carbonyl]-5-(2-pyridinylamino)pentyl]-2-naphthalenesulfonamide A. (S)-N-[1-[(4-Methyl-1-piperidinyl)carbonyl]-3-oxopropyl]-2-naphthalenesulfonamide To a solution of 3.87 g (9.91 mmol) of Example 3 Part D alcohol in 100 mL of dry methylene chloride (distilled from phosphorous pentoxide) at room temperature was added 4.62 g (10.9 mmol) of Dess-Martin periodinane then after 5 minutes 1.2 mL (15 mmol) of pyridine. The reaction mixture was stirred for 45 minutes then added was 300 mL of ether and 300 mL of saturated aqueous sodium bicarbonate solution containing 12 g of sodium thiosulfate. The mixture was stirred rapidly, the organic layer was separated and the aqueous layer was extracted with two-100 mL portions of ether. The organic layers were combined, washed with 250 mL of saturated aqueous sodium bicarbonate solution, 250 mL of 1M aq HCl solution, 250 mL of brine, dried (magnesium sulfate) and concentrated in vacuo to give a crude yellow oil. The crude material was purified by flash chromatography (Merck silica, 150×100 mm, 2:1 ethyl acetate/hexane) to afford 3.26 g (8.39 mmol, 85%) of title compound as a foam.

B. (S)-6-(4-Methyl-1-piperidinyl)-5-[(2-naphthalenylsulfonyl)amino]-6-oxo-2-hexenoic acid, methyl ester To a solution of 4.58 g (11.8 mmol) of Part A compound in 100 mL of THF (distilled from sodium/benzophenone) was added 3.94 g (11.8 mmol, Aldrich) of methyl(triphenylphosphoranylidene)acetate at room temperature. The reaction mixture was stirred for 16 h then concentrated in vacuo to give an orange oil. The crude material was purified by flash chromatography (Merck silica, 150×100 mm, 1:2 ethyl acetate/hexane) to afford 4.58 g (10.3 mmol, 88%) of title compound as a foam.

C. (S)-4-Methyl-6-[(2-naphthalenylsulfonyl)amino]-ε-oxo-1-piperidinehexanoic acid, methyl ester A mixture of 4.54 g (10.2 mmol) of Part B compound and 454 mg of 10% palladium on carbon catalyst (Aldrich) in 80 mL of ethyl acetate was stirred under an atmosphere of hydrogen (balloon) for 16 h. The reaction mixture was passed through a 0.4 μM polycarbonate membrane filter to remove the catalyst and the filtrate was concentrated in vacuo to afford an oil. The crude material was purified by flash chromatography (Merck silica, 100×80 mm, 1:1 ethyl acetate/hexane) to afford 4.50 g (10.3 mmol, quantitative) of title compound as a foam.

D. (S)-N-[5-Hydroxy-1-[(4-methyl-1-piperidinyl)carbonyl]pentyl]-2-naphthalenesulfonamide To a slurry of 98 mg (4.5 retool, Aldrich) of lithium borohydride in 50 mL of anhydrous ether (Mallinckrodt) was added at room temperature 180 μL (4.5 mmol) of methanol dropwise over 10 minutes. The mixture was stirred for 40 minutes until bubbling ceased then a solution of 500 mg (1.21 mmol) of Part C ester in 30 mL of anhydrous ether was added dropwise over 15 minutes. The reaction mixture was stirred for 16 h then quenched by dropwise addition of 1 mL of 0.5M aq HCl solution, stirred until clear then concentrated in vacuo to give a white solid. The solid was partitioned between 50 mL of ethyl acetate and 50 mL of 1M aq HCl solution. The aqueous layer was separated and extracted with two-50 mL portions of ethyl acetate. The organic layers were combined, dried (magnesium sulfate) and concentrated in vacuo to give an oil. The crude material was purified by flash chromatography (Merck silica, 100×50 mm, 2:1 ethyl acetate/hexane) to afford 300 mg (0.72 mmol, 59%) of title compound as a white foam.

E. (S)-N-[1-[(4-Methyl-1-piperidinyl)carbonyl]-5-oxopentyl]-2-naphthalenesulfonamide To a solution of 300 mg (0.72 mmol) of Part D alcohol in 10 mL of dry methylene chloride (distilled from phosphorous pentoxide) at room temperature was added 456 mg (1.08 mmol) of Dess-Martin periodinane then after 5 minutes 0.12 mL (1.4 mmol) of pyridine. The reaction mixture was stirred for 20 minutes then added was 30 mL of ether and 30 mL of saturated aqueous sodium bicarbonate containing 1.2 g of sodium thiosulfate. The mixture was stirred rapidly, the organic layer was separated and the aqueous layer was extracted with two-30 mL portions of ether. The organic layers were combined, washed with two-50 mL of saturated aqueous sodium bicarbonate solution, 100 mL of 1M aq HCl solution, 100 mL of brine, dried (magnesium sulfate) and concentrated in vacuo to give a solid. The crude material was purified by flash chromatography (Merck silica, 50×25 mm, ethyl acetate) to afford 273 mg (0.65 mmol, 91%) of title compound as a white foam.

F. (S)-N-[1-[(4-Methyl-1-piperidinyl)carbonyl]-5-(2-pyridinylimino)pentyl]-2-naphthalenesulfonamide A solution of 206 mg (0.50 mmol) of Part E compound and 70 mg (0.74 mmol, Aldrich) of 2-aminopyridine in 5 mL of toluene (Burdick and Jackson) was refluxed under a Dean-Stark apparatus for 5 h. The reaction mixture was cooled and concentrated in vacuo to give a yellow oil. The crude material was purified by flash chromatography (Merck silica, 120×15 mm, 1:1 ethyl acetate/hexane) to afford 60 mg (0.12 retool, 24%) of title compound as a colorless oil.

G. (S)-N-[1-[(4-Methyl-1-piperidinyl)carbonyl]-5-(2-pyridinylamino)pentyl]-2-naphthalenesulfonamide To a solution of 50 mg (0.10 mmol) of Part F compound in 1 mL of THF (distilled from sodium/benzophenone) was added 10 mg (0.45 mmol, Aldrich) of lithium borohydride at room temperature. The reaction mixture was stirred for 3.5 h then quenched by dropwise addition of ~2 mL of 1M aq HCl solution. The resulting mixture was partitioned between 10 mL of saturated sodium bicarbonate solution and 10 mL of methylene chloride. The aqueous layer was separated and extracted with an additional 10 mL of methylene chloride. The organic layers were combined, dried (sodium sulfate) and concentrated in vacuo to give an oil. The oil was solubilized in 2 mL of acidic methanol (prepared by addition of 0.10 mL of acetyl chloride to 2 mL of methanol) then after 5 minutes concentrated in vacuo; added to the residue was 2 mL of fresh methanol and concentrated, repeated twice to remove boron impurities. The residue was partitioned between 10 mL of saturated sodium bicarbonate solution and 10 mL of methylene chloride. The aqueous layer was separated and extracted with an additional 10 mL of methylene chloride. The organic layers were combined, dried (sodium sulfate) and concentrated in vacuo to give an oil. The crude material was purified by flash chromatography (Merck silica, 120×15 mm, 1:99 methanol/ethyl acetate) to afford 42 mg (0.085 mmol, 85%) of title compound as a colorless oil. The oil was crystallized (ethyl acetate/hexane) to give 28 mg (0.057 mmol, 57%) of title compound as a white solid, mp 127°–129°.

Analysis calcd for $C_{27}H_{34}N_4O_3S$: C, 65.56; H, 6.93; N, 11.33; S, 6.48
Found: C, 65.38; H, 6.91; N, 11.28; S, 6.36.

EXAMPLE 5

(S)-N-[1-[(4-Methyl-1-piperidinyl)carbonyl]-4-(2-pyrimidinylaminobutyl]-2-naphthalenesulfonamide A. (S)-β-[[(1,1-Dimethylethoxy)carbonyl]amino]-4-methyl-α-oxo-1-piperidinepentanoic acids, phenylmethyl ester To a clear solution of 8.00 g (23.7 mmol, Bachem) of N-Boc-L-glutamic acid-γ-benzyl ester, in 150 mL of DMF was added 3.1 mL (26 mmol, Aldrich) of 4-methylpiperidine and 4.0 g (26 mmol,Schweizerhall) of 1-hydroxybenzotriazole monohydrate. The mixture was cooled to 0° C. and treated with 5.2 mL (47 mmol, Aldrich) of N-methylmorpholine, followed by the addition of 5.0 g (26 mmol, Bachem) of WSC. The mixture was stirred at 0° C. for 2 hrs and at r.t. for 4 hrs. The mixture was concentrated in high vacuum. The residue was worked up with 300 mL of EtOAc, washed with 200 mL of 1N HCl and 200 mL of a saturated aqueous solution of NaHCO₃, H₂O and brine; dried (MgSO₄) and concentrated in vacuo to afford 9.92 g (23.7 mmol, 100%) of title compound as a clear oil.

B. (S)-β-[Bis[(1,1-dimethylethoxy)carbonyl]-4-methyl-α-oxo-1-piperidinepentanoic acid, phenylmethyl ester To a syrup of 6.50 g (15.5 mmol) of Part A compound in 1.0 mL of acetonitrile was added 1.38 g (9.3 mmol, Aldrich) of 4-pyrrolidinopyridine and treated with 43.4 g (199 mmol, Fluka) of ditertbutyl dicarbonate dropwise over a period of 6 hrs at 87° C. The resulting black light oil was purified by flash chromatography (280 g, Merck silica gel, 15% EtOAc/hexane) to afford pure 4.7 g (9.0 mmol, 60%) of title compound as a clear oil.

C. (S)-[4-Hydroxy-1-[(4-methyl-1-piperidinyl)carbonyl]butyl]imidodicarbonic acid, bis-(1,1-dimethylethyl)ester A light yellow solution of 4.4 g (8.5 mmol) of Part B compound in 50 mL (Aldrich) anhydrous EtOH was treated with 1.44 g (34 mmol, Aldrich) of lithium chloride. The slurry was allowed to stir at r.t. for 15 min. until the solid was completely dissolved. The yellow solution was treated with 642 mg (17 mmol, Aldrich) of sodium borohydride. The mixture was stirred at r.t. for 26 hrs. The mixture was treated then with a second portion of 1.44 g (34 mmol, Aldrich) of lithium chloride and 642 mg (17 mmol, Aldrich) of sodium borohydride. After stirred at r.t. 24 hrs, the mixture was treated with a third portion of 1.44 g (34 mmol, Aldrich) of lithium chloride and 642 mg (17 mmol, Aldrich) of sodium borohydride and allowed to stir for 24 hrs. The crude reaction mixture was quenched with 10 mL of H₂O. The mixture was concentrated in vacuo. The residue was partitioned between 100 mL of 0.5N HCl and 200 mL of EtOAc. The organic layer was separated and washed with 100 mL of a saturated aqueous solution of NaHCO₃ and brine; dried (MgSO₄) and concentrated in vacuo. The residue was purified by flash chromatrography (100 g, Merck silica gel, 40% EtOAc/hexane) to afford 2.5 g (6.0 mmol, 71%) of pure title compound as a clear oil.

D. (S)-[1-[(4-Methyl-1-piperidinyl)carbonyl]-4-[(methylsulfonyl)oxy]butyl]imidodicarbonic acid, bis(1,1-dimethylethyl) ester A clear solution of 2.5 g (6.0 mmol) of Part C compound in 10 mL of CH₂Cl₂ (distilled from P₂O₅) was cooled to −20° C. and treated with 1.3 mL (9.0 mmol) of triethylamine (Et₃N) (distilled from CaH₂), followed by the addition of 0.60 mL (7.3 mmol, Aldrich) of methanesulfonyl chloride. The mixture was stirred at −20° for 1 hr. The crude mixture was diluted with 20 mL of CH₂Cl₂, washed with 20 mL of 1N HCl and 20 mL of a saturated aqueous solution of NaHCO₃ and brine; dried (MgSO₄), and concentrated in vacuo to afford 2.9 g (5.9 mmol, 97%) of title compound.

E. (S)-[4-Iodo-1-[(4-methylpiperidinyl)carbonyl]butyl]imidodicarbonic acid, bis-(1,1-dimethylethyl)ester To the light yellow solution of 2.8 g (5.6 mmol) of Part D compound in 60 mL of acetone (Burdick and Jackson) was added 4.2 g (28 mmol) of sodium iodide. The mixture was stirred in the dark at r.t. for 16 hrs. The crude reaction mixture was concentrated in vacuo. The residue was diluted with EtOAc, washed with 200 mL aqueous 5% sodium thiosulfate and an aqueous solution of saturated NaHCO₃ and brine; dried (MgSO₄) and concentrated in vacuo to give 2.73 g (5.20 mmol, 93%) of title compound.

F. (S)-[4-Azido-1-[(4-methylpiperidinyl)carbonyl]butyl]imidodicarbonic acid, bis(1,1-dimethylethyl) ester A light yellow solution of 2.7 g (5.2 mmol) of Part E compound in 12 mL of DMF (Burdick and Jackson) was treated with 940 mg (14.4 mmol, Aldrich) of sodium azide at r.t. for 1 hr. The crude reaction mixture was filtered. The filtrate was concentrated in vacuo. The residue was diluted with 50 mL of Et₂O and 50 mL of H₂O. The organic layer was separated and washed with a 5% aqueous solution of sodium thiosulfate, dried (MgSO₄), concentrated in vacuo to give 2.3 g of crude product as a clear oil. The crude product was purified by flash chromatography (100 g, Merck silica gel, 10% EtOAc/hexane) to afford 2.4 g (5.4 mmol, 100%) of title compound.

G. (S)-[4-Amino-1-[(4-methylpiperidinyl)carbonyl]butyl]imidodicarbonic acid, bis(1,1-dimethylethyl) ester To the solution of 2.4 g (5.4 mmol) of Part F compound in 13 mL of methanol (Burdick and Jackson) was added 344 mg of 10% palladium on activated carbon (Aldrich). The mixture was stirred under an atmosphere of hydrogen (balloon) for 3 hrs. The crude mixture was filtered through a (Millipore, type FH 0.5 μm) polycarbonate membrane. The filtrate was concentrated in vacuo to give 2.2 g (5.3 mmol, 100%) of title compound.

H. (S)-[1-[(4-Methyl-1-piperidinyl)carbonyl]-4-(2-pyrimidinylamino)butyl]imidodicarbonic acid, bis(1,1-dimethylethyl) ester A clear solution of 1.0 g (2.4 mmol) of Part G compound in 2 mL of anhydrous EtOH (Aldrich) was treated with 830 mg (7.3 mmol, Janssen) of 2-chloropyrimidine followed by the addition of 406 mg (4.8 mmol, Mallinckrodt) of sodium bicarbonate. The mixture was stirred at 65° for 17 hrs. The crude reaction mixture was concentrated in vacuo. The residue was diluted with 2 mL of EtOAc and 20 mL of Et₂O. The solid was removed by suction filtration. The filtrate was concentrated in vacuo. The resulting oil was dissolved in 20 mL EtOAc washed with 50 mL of aqueous saturated solution of sodium bicarbonate and brine; dried (MgSO₄) concentrated in vacuo. The resulting crude product was purified by flash chromatography (13 g, Merck silica gel, 40% EtOAc/hexane) to afford 625 mg (1.3 mmol, 53%) of title compound.

I. (S)-2-Amino-1-(4-methyl-1-piperidinyl)-5-(2-pyrimidinylamino)-1-pentanone, dihydrochloride The clear solution of 625 mg (1.30 mmol) of Part H compound in 5 mL of 1,4-dioxane (Burdick and Jackson) was treated 3.2 mL (4M in dioxane, 13 mmol, Aldrich) of HCl solution at r.t. for 19 hrs. The mixture was concentrated in vacuo to give 472 mg (1.6 mmol, 100%) of title compound.

J. (S)-N-[1-[(4-Methyl-1-piperidinyl)carbonyl]-4-(2-pyrimidinylamino)butyl]2-naphthalenesulfonamide A clear solution of 323 mg (1.4 mmol, Aldrich) of 2-naphthalenesulfonyl chloride in 5 mL of $CH_2Cl_2$ (distilled from $P_2O_5$) was cooled to 0° and treated with 0.63 mL (4.5 mmol) of $Et_3N$ (distilled from $CaH_2$), followed by the addition of a solution of 472 mg (1.3 mmol) of Part I compound in 5 mL of $CH_2Cl_2$ (distilled from $P_2O_5$). This addition was done dropwise keeping the temperature below 5°. The reaction mixture was stirred at 0° for 4 hrs. The crude reaction mixture was washed with 30 mL of a saturated aqueous solution of $NaHCO_3$, brine; dried ($MgSO_4$), and concentrated in vacuo. The crude product was purified by flash column chromatography (20 g, Merck silica gel, 50% EtOAc/hexane) to give a solid. The solid was recrystallized from $Et_2O$ to afford 337 mg (0.70 mmol, 54%) of title compound as a white solid, m.p. 98°–100° (softens at 68°)

Analysis Calc'd for $C_{25}H_{31}N_5O_3S.0.57 H_2O$: C, 61.04; H, 6.59; N, 14.24; S, 6.52

Found: C, 61.26; H, 6.33; N, 14.02; S, 6.59.

(S)-N-[1-[(4-Methyl-1-piperidinyl)carbonyl]-4-(2-pyrazinylamino)butyl]-2-naphthalenesulfonamide A. (S)-[1-[(4-Methyl-1-piperidinyl)carbonyl]-4-(2-pyrazinylamino)butyl]imidodicarbonic acid, bis(1,1-dimethylethyl) ester A mixture of 475 mg (1.15 mmol) of Example 5 Part G amine, 786 mg (6.89 mmol, Janssen) of 2-chloropyrazine and 580 mg (6.90 mmol, Mallinckrodt) of sodium bicarbonate in 2 mL of reagent 1-butanol was heated to 120° for 14 h. The reaction mixture was cooled, concentrated in vacuo and the residue was partitioned between 15 mL of ethyl acetate and 15 mL of water. The organic layer was separated, dried (sodium sulfate) and concentrated in vacuo to give a crude yellow oil. The crude material was purified by flash chromatography (Merck silica, 12×3.0 cm, ethyl acetate) to afford 195 mg (0.40 mmol, 35%) of title aminopyrazine as a pale yellow oil.

B. (S)-N-[1-[(4-Methyl-1-piperidinyl)carbonyl]-4-(2-pyrazinylamino)butyl]-2-naphthalenesulfonamide To a solution of 190 mg (0.39 mmol) of Part A aminopyrazine in 1 mL of dioxane was added at room temperature 2.0 mL (4M in dioxane, 8 mmol, Aldrich) of HCl solution. The reaction mixture was stirred for 18 h (precipitate formed) then concentrated in vacuo to give the crude deprotected amine hydrochloride as a yellow solid. The crude material was suspended in 2 mL of methylene chloride (distilled from phosphorous pentoxide) then cooled to 0° and added in one portion was 250mL (1.8 mmol, distilled from calcium hydride) of triethylamine followed by dropwise addition of a solution of 88 mg (0.39 mmol, Aldrich) of 2-naphthalenesulfonyl chloride in 1 mL of methylene chloride. The reaction mixture was stirred for 15 minutes then partitioned between 15 mL of ethyl acetate and 15 mL of water. The aqueous layer was separated and extracted with an additional 10 mL of ethyl acetate. The organic layers were combined, dried (sodium sulfate) and concentrated in vacuo to give an oil. The crude material was purified by flash chromatography (Merck silica, 14×3.0 cm, 1:99 methanol/ethyl acetate) to afford 107 mg (0.22 mmol, 57%) of title compound as a solid white foam.

Analysis calcd for $CH_{25}H_{31}N_5O_3S \rightleftharpoons 0.36H_2O$: C, 61.53; H, 6.55; N, 14.35; S, 6.57.

Found: C, 61.98; H, 6.48; N, 13.90; S, 6.77.

EXAMPLE 7

(S)-7-Methoxy-N-[1-[(4-methyl-1-piperidinyl)carbonyl-4-(2-pyridinylamino)butyl]-2-naphthalenesulfonamide A. 2-[Bis[(1,1-dimethylethoxy))carbonyl]amino]-1-(4-methyl-1-piperidinyl)-5-[(1-oxo -2-pyridinyl)amino]-1-pentanone A clear solution of 2.0 g (4.8 mmol) of Example 5, Part G compound in 16 mL of n-butanol was treated with 1.61 g (9.7 mmol,Aldrich) of 2-chloropyridine N-oxide hydrochloride followed by the addition of 1.63 g (19.4 mmol,Mallinckrodt) of sodium bicarbonate. The mixture was stirred at 100° for 21 hrs. The crude reaction mixture was filtered. The filtrate was concentrated in vacuo. The residue was diluted in 100 mL of EtOAc; washed with brine; dried ($MgSO_4$) and concentrated in vacuo. The resulting crude product was purified by flash chromatography (60 g,Merck silica gel, 5% MeOH/EtOAc) to afford 1.16 g (2.3 mmol, 47%) of title compound as a clear oil.

B. 2-[Bis[(1,1-dimethylethoxy) carbonyl]amine,]-1-(4-methyl-1-piperidinyl)-5-(2-pyridinylamino)-1-pentanone A solution of 1.11 g (2.2 mmol) of Part A compound in 45 mL of absolute EtOH (Pharmco) was treated with 690 mg (11 mmol,Aldrich) of ammonium formate and 1.0 g of palladium on activated carbon (Aldrich). The reaction mixture was refluxed for 1.5 hrs. The crude reaction mixture was filtered through a (Millipore, type FH 0.5 μm) polycarbonate membrane. The filtrate was concentrated in vacuo. The crude product was purified by flash chromatography (60 g, Merck silica gel, 50% EtOAc/hexane) to afford 641 mg (1.3 mmol, 60%) of title compound as a heavy syrup.

C. 2-Amino-1-(4-methyl-1-piperidinyl)-5-(2-pyridinylamino)-1-pentanone, dihydrochloride The clear solution of 625 mg (1.3 mmol) of Part B compound in 5 mL of 1,4-dioxane (Burdick and Jackson) was treated with 3.2 mL (4 M in dioxane, 13.0 mmol, Aldrich) of HCl solution at room temperature for 24 hrs. The crude reaction mixture was concentrated in vacuo to afford 479 mg (1.32 mmol, 100%) of title compound as a white solid.

D. 2-Methoxynaphthalene-7-sulfonyl chloride (1) 2-Methoxynaphthalene-7-sulfonic acid, sodium salt To a slurry of 10.0 g (40.6 mmol) of 2-naphthol-7-sulfonic acid, sodium salt in 60 mL of 2:1 water/ethanol was added 1.79 g (44.7 mmol) of sodium hydroxide pellets at room temperature. The mixture was stirred until homogeneous then added in one portion was 5.63 g (44.7 mmol, Aldrich) of dimethylsulfate. A precipitate formed after 15 minutes. The reaction mixture was stirred for 18 hours then concentrated in vacuo. The residue was slurried with −150 mL of absolute ethanol then filtered. The solid was collected on a Buchner funnel and dried to give 10.5 g of crude product. The crude material was slurried with 100 mL of 95% ethanol, heated to reflux then allowed to cool to room temperature. The resulting mixture was filtered on a Buchner funnel. The solid was collected and dried in vacuo to afford 9.16 g (35.2 mmol, 87%) of title compound as a pale brown solid.

(2). 2-Methoxynaphthalene-7-sulfonyl chloride

To a mixture of 3.00 g (11.5 mmol) of Part (1) compound and 4.8 mL (52 mmol) of phosphorous oxychloride was added 3.00 g (14.4 mmol, Aldrich) of phosphorous pentachloride at room temperature. The mixture was warmed gently until homogeneous (bubbling) then heated to reflux (bath temperature 125°) for 4 hours. The resulting dark reaction mixture was cooled in an ice-bath, added slowly to 30 g of ice-water then extracted with 50 mL of chloroform. The chloroform extract was washed with 25 mL of water, 25 mL of saturated aqueous sodium bicarbonate solution, dried (magnesium sulfate) and concentrated in vacuo to give an oil. The crude material was purified by flash chromatography (Merck silica, 12×3.0 cm, methylene chloride) to afford 1.58 g (6.16 mmol, 54%) of title compound as a pale brown solid.

E. (S)-7-Methoxy-N-[1-[(4-methyl-1-piperidinyl)carbonyl]-4-(2-pyridinylamino)butyl]-2-naphthalenesulfonamide A white slurry of 150 mg (0.41 mmol) of Part C compound in 3 mL of $CH_2Cl_2$ (distilled from $P_2O_5$) was cooled to 0° and treated with 230 μL (1.65 mmol) of $Et_3N$ (distilled from $CaH_2$) followed by the dropwise addition of a solution of 117 mg (0.46 mmol) of Part D compound in 3 mL of $CH_2Cl_2$, keeping the temperature below 5°. The reaction mixture was stirred at 0° for 3 hrs. The crude reaction mixture was diluted in 50 mL $CH_2Cl_2$; washed with a saturated aqueous solution of $NaHCO_3$, and brine; dried ($MgSO_4$) and concentrated in vacuo. The crude product was purified by flash chromatography (13 g, 60 Merck silica gel; 100% EtOAc) to afford 151 mg (0.296 mmol, 74%) of title compound as a white foam.

Analysis calcd. for $C_{27}H_{34}N_4O_4S$: C,63.51; H,6.71; N,10.97; S,6.28.

Found: C,63.38; H,6.71; N,10.87; S,6.26.

EXAMPLE 8

(S)-5-(Dimethylamino)-N-[1-[(4-methyl-1-piperidinyl)carbonyl]-4-(2-pyridinylamino)butyl]-1-naphthalenesulfonamide A white slurry of 150 mg (0.41 mmol) of Example 7, Part C compound in 3 mL of $CH_2Cl_2$ (distilled from $P_2O_5$) was cooled to 0° and treated with 230 μL of $Et_3N$ (1.65 mmol) (distilled from $CaH_2$ followed by the dropwise addition solution of 123 mg (0.5 mmol, Aldrich) of dansyl chloride in 3 mL of $CH_2Cl_2$, keeping the temperature below 5°. The yellow reaction mixture was allowed to stir at 0° for 3 hrs. The crude reaction mixture was concentrated in vacuo. The residue was diluted in EtOAc. The $Et_3N \cdot HCl$ precipitate was removed by suction filtration. The filtrate was washed with brine; dried ($MgSO_4$) and concentrated in vacuo. The crude product was purified by flash chromatography (12 g, 60 Merck silica gel; 90% EtOAc/hexane) to afford 212 mg (0.404 mmol, 98%) of title compound as a yellow foam.

Analysis calcd. for $C_{28}H_{37}N_5O_3S$: C,64.22; H,7.12; N,13.37; S,6.12

Found: C,64.07; H,7.17; N,12.99; S,6.01.

EXAMPLE 9

(S)-3-Methyl-N-[1-[(4-methyl-1-piperidinylcarbonyl]-4-(2-pyridinylaminobutyl]-8-quinolinesulfonamide To a solution of 225 mg (0.62 mmol) of Example 7, Part C amine dihydrochloride in 2 mL of methylene chloride (distilled from phosphorous pentoxide) cooled to 0° was added 350 μL (2.5 mmol, distilled from calcium hydride) of triethylamine then 149 mg (0.62 mmol) of 3-methyl-8-quinolinesulfonylchloride in one portion. The reaction mixture was stirred for 20 minutes then partitioned between 20 mL of ethyl acetate and 20 mL of saturated aq sodium bicarbonate solution. The organic layer was separated and the aqueous layer was extracted with an additional 10 mL of ethyl acetate. The combined organic extracts were dried (sodium sulfate) and concentrated in vacuo to give an oil. The crude material was purified by flash chromatography (Merck silica, 12×3.0 cm, 1:3 acetone/toluene) to afford 190 mg (0.38 mmol, 62%) of title compound as a solid white foam.

Analysis calcd for $C_{26}H_{33}N_5O_3S \cdot 0.14H_2O$: C, 62.68; H, 6.73; N, 14.06; S, 6.44

Found: C, 63.12; H, 6.84; N, 13.62; S, 6.06.

EXAMPLE 10

1,2,3,4-Tetrahydro-3-methyl-N-[(S)-1-[(4-methyl-1-piperidinyl)carbonyl]-4-(2-pyridinylamino)butyl]-8-quinolinesulfonamide, 2:1 mixture of 3-methyl isomers To a solution of 132 mg (0.27 mmol) of Example 9 quinoline in 4 mL of methanol (Burdick and Jackson) was added 132 mg of palladium black catalyst (Aldrich). The reaction mixture was stirred under an atmosphere of hydrogen (balloon) for 20 hours at room temperature then filtered through a 0.4 μM polycarbonate membrane to remove the catalyst. The filtrate was concentrated in vacuo to give an oil. The crude material was purified by flash chromatography (Merck silica, 15×1.5 cm, 4:1 ethyl acetate/hexane) to afford 80 mg (0.16 mmol, 59%) of title compound as a solid white foam.

Analysis calcd for $C_{26}H_{37}N_5O_3S$: C, 62.50; H, 7.46; N, 14.02; S, 6.42

Found: C, 62.60; H, 7.44; N, 13.64; S, 6.44.

EXAMPLE 11

A. (2R-trans)-4-Methyl-2-piperidinecarboxylic acid
(1) 4-Methyl-2-piperidinecarbonitrile To 500 g of sodium hypochlorite solution (5% in Cl, Aldrich) cooled in an ice-bath was added dropwise 33.6 g (340 mmol, Aldrich) of 4-methylpiperidine over 40 minutes. The reaction mixture was stirred for 20 minutes then poured into a separatory funnel and extracted with two-400 mL portions of ether. The ether extracts were combined, dried (sodium sulfate) and concentrated in vacuo to give ~44 g of N-chloro intermediate as a yellow liquid.

To a solution of 19.1 g (340 mmol) of potassium hydroxide in 140 mL of 95% ethanol heated to 80° was added dropwise over 40 minutes a solution of the crude N-chloropiperidine from above in 20 mL of 95% ethanol- The addition was mildly exothermic and a precipitate formed. The reaction mixture was stirred for 10 minutes, cooled to room temperature then concentrated in vacuo and to the residue was added 85 mL of 2N aq NaOH solution. The resulting mixture was extracted with three-75 mL portions of ether. The ether extracts were combined, dried (sodium sulfate) and concentrated in vacuo to give the crude imine as a viscous yellow oil.

To a solution of 110 g (1.7 mol, Mallinckrodt) of potassium cyanide in 400 mL of water cooled in an ice-bath was added over ~1 h 183 mL (2.20 mol) of concentrated HCl then the crude imine from above. The reaction mixture was stirred between 10-20° for 4 h then cooled in an ice-bath and basified to pH 12 by addition of ~80 g of potassium hydroxide pellets. The resulting solution was poured into a separatory funnel and extracted with three-300 mL portions of ether. The ether layers were combined, dried (sodium sulfate) and concentrated in vacuo to give a yellow oil. The crude material was purified by simple distillation at reduced pressure to afford 13.2 g (106 mmol, 31%) of title nitrite as a clear liquid, bp 72-74° (3 mm).

(2) 4-Methyl-2-piperidinecarboxylic acid, ethyl ester

To 250 mL of 6N aq HCl solution was added 13.0 g (105 mmol) of Part (1) nitrite at room temperature. The reaction mixture was heated to reflux (bath temp 145°) for 6 h then cooled to room temperature and concentrated in vacuo to give the crude acid hydrochloride as a solid.

To 250 mL of absolute ethanol cooled in an ice-bath was added dropwise 40 mL (550 mmol) of thionyl chloride over 30 minutes. The solution was stirred for an additional 15 minutes then added to the crude acid hydrochloride from above. The resulting slurry was heated to reflux for 4 h then cooled to room temperature and filtered to remove solids. The filtrate was concentrated in vacuo to give the crude ester amine hydrochloride as brown oil. The oil was partitioned between 150 mL of saturated aq potassium carbonate solution and 150 mL of chloroform. The aqueous layer was separated and extracted with two-100 mL portions of chloroform. The organic extracts were combined, dried (sodium sulfate) and concentrated to give crude title ester as a brown oil. The crude material was purified by distillation through a 10 cm packed column (glass helices, 3 mm) at reduced pressure to afford 11.0 g (64.3 mmol, 61%) of title ester as a colorless liquid, bp 37-38° (0.4 mm). The trans/cis ratio was determined as ~6:1 by 270 MHz $^1$H NMR.

(3) (4R)-4-Methyl-1-[(phenylmethoxy)carbonyl]-2-piperidinecarboxylic acid, ethyl ester To a solution of 10.0 g (58.5 mmol) of Part (2) amine in 100 mL of methylene chloride cooled to 0° was added 9.8 mL (70 mmol, distilled from calcium hydride) of triethylamine in one portion then dropwise 11.9 g (70 mmol, Aldrich) of benzyl chloroformate over 20 minutes. The reaction mixture was stirred for 30 minutes then washed with 100 mL of 1N aq HCl, 100 mL of saturated aq sodium bicarbonate solution, 50 mL of brine, dried (magnesium sulfate) and then concentrated in vacuo to give an oil. The crude oil was purified by flash chromatography (Merck silica, 30×10 cm, 600 g, 1:9 EtOAc/hexane) to afford 12.7 g (41.6 mmol, 71%) of title compound (trans isomer) as e colorless oil. In addition, 2.95 g (9.67 mmol, 17%) of a ~1:1 mixture of trans/cis title compound was obtained as a colorless oil.

(4) (4R)-4-Methyl-1-[(phenylmethoxy)carbonyl]-2-piperidinecarboxylic acid

To a solution of 8.95 g (29.3 mmol) of Part (3) compound in 90 mL of absolute ethanol cooled in an ambient water bath was added 90 mL of 1N aq NaOH solution. The reaction mixture was stirred for 16 h then concentrated in vacuo to ~½ volume to remove ethanol. The residue was partitioned between 100 mL of 1M aq HCl solution and 100 mL of ether. The aqueous layer was separated and extracted with two-50 mL portions of ether. The ether extracts were combined, dried (magnesium sulfate) and concentrated in vacuo to afford 8.15 g (29.4 mmol, 100%) of title compound as a colorless oil.

(5) (4R)-4-Methyl-2-piperidinecarboxylic acid

To a solution of 8.14 g (29.3 mmol) of Part (4) compound in 135 mL of 90% aq EtOH was added 600 mg of 10% palladium on carbon catalyst (Aldrich).

The resulting mixture was stirred under an atmosphere of hydrogen (balloon) for 16 h then filtered through paper on a Buchner funnel. The filtrate was passed through a 0.4 μM polycarbonate membrane then concentrated in vacuo to give a white solid. The crude material was dissolved in water then freeze-dried to afford 4.15 g (29.0 mmol, 99%) of title compound as a racemic mixture in the form of a white solid.

(6) (2R-trans)-4-Methyl-2-piperidinecarboxylic acid

A slurry of 4.0 g (28.7 mmol) of Part (5) racemic mixture and 85 mL of 95% aq EtOH was warmed then 4.30 g (28.7 mmol, Aldrich) of L-tartaric acid was added and the mixture heated to reflux until homogeneous. The resulting solution was allowed to cool to room temperature and stand overnight. The solids which formed were collected on a Buchner funnel, washed with cold absolute EtOH and dried under vacuum to give 3.98 g of product as small white crystals. Recrystallization (90% aq EtOH, ~75 mL) afforded 3.45 g (11.8 mmol, 41%) of L-tartaric acid salt as large white crystals, mp 193-195°.

A solution of 3.39 g (11.6 mmol) of the above salt in aq EtOH was placed on an ion exchange column (5×5 cm, washed Bio-Rad AG-MP50, 100 mL) and eluted with 300 mL of water then 1000 mL of 4% aq conc ammonium hydroxide. The product containing fractions were combined, concentrated in vacuo to ~½ volume then freeze-dried to afford 1.66 g (11.6 mmol, 41% from Part (5) racemic mixture) of chiral title compound as a white solid.

B. (2S-trans)-4-Methyl-2-piperidinecarboxylic acid,

Absolute ethanol (50 mL, Pharmco) was cooled to 0° and treated dropwise with 4.6 mL (63 mmol, Aldrich) of thionyl chloride over a period of 5 min and stirred at 0° for 20 min. The clear mixture was treated with a solution of 3.0 g (21 mmol) of Part A compound in absolute ethanol and refluxed for 4 hrs. The crude reaction mixture was allowed to cool to r.t. and concentrated in vacuo. The residue was partitioned between 150 mL of CHCl$_3$ and 50 mL of a saturated aqueous solution of potassium carbonate. The organic layer was separated and dried (Na$_2$SO$_4$) and concentrated in vacuo to afford 4.0 g (23 mmol, 100%) of pure title compound as an oil.

C. (2R-trans)-1-[N-[(1,1-Dimethylethoxy)carbonyl]-O-(phenylmethyl)-L-α-glutamyl]-4-methyl-2-piperidinecarboxylic acid, ethyl ester To a yellow solution of 6.41 g (19.0 mmol, Bachem) of N-Boc-L-glutamic acid-β-benzyl ester, in 90 mL of DMF (Burdick & Jackson) was added 3.6 g (21 mmol) of Part B compound, and 3.2 g (21 mmol, Schweizerhall) of 1-hydroxybenzotriazole monohydrate. The mixture was cooled to 0° and treated with 4.2 mL (38 mmol, Aldrich) of 4-methylmorpholine, followed by the addition of 4.0 g (21 mmol, Bachem) of 1-(3-dimethylaminopropyl)-3-ethylcarbodiimide hydrochloride (WSC). The mixture was stirred at 0° for 3 hrs and at room temperature for 17 hrs. The mixture was concentrated in high vacuum. The residue was diluted with 100 mL of EtOAc, washed with 100 mL of 1N HCl and 100 mL of a saturated aqueous solution of NaHCO₃ and brine; dried (MgSO₄) and concentrated in vacuo to afford 8.9 g (18 mmol, 90%) of title compound as a yellow oil.

D. (2R-trans)-1-[N,N-Bis[(1,1-dimethylethoxy)carbonyl]-O-(phenylmethyl)-L-α-glutamyl]-4-methyl-2-piperidinecarboxylic acid, ethyl ester To the yellow oil of 8.5 g (17 mmol) of Part C compound was added 5 drops of acetonitrile and 1.54 g (10.4 mmol, Aldrich) of 4-pyrrolidinopyridine and treated with 49 g (225 mmol, Bachere) of ditertbutyldicarbonate dropwise over a period of 4 hrs at 90°. The crude product was purified by flash chromatography (30 g, Merck silica gel, 45% EtOAc/hexane) to afford 10 g (17 mmol, 98%) of title compound as a yellow oil.

E. (2R-trans)-1-[N,N-Bis[(1,1-dimethylethoxy)carbonyl]-L-α-glutamyl]-4-methyl-2-piperidinecarboxylic acid, ethyl ester To the yellow solution of 5.0 g (8.5 mmol) of Part D compound in 50 mL of methanol (Baker) was added 1.0 g of 10% palladium on activated carbon (Aldrich). The mixture was stirred under an atmosphere of hydrogen (balloon) for 17 hrs. The crude mixture was filtered through a (Millipore, type FH 0.5 μm) polycarbonate membrane. The filtrate was concentrated in vacuo to give 4.0 g (8.0 mmol, 95%) of title compound as a heavy syrup.

F. (2R-trans)-1-[N,N-Bis[(1,1-dimethylethoxy)carbonyl]-O-(4-nitrophenyl)-L-α- glutamyl]-4-methyl-2-piperidinecarboxylic acid, ethyl ester To a clear solution of 3.5 g (7.0 mmol) of Part E compound in 50 mL of DMF (Burdick and Jackson) was added 2.0 g (14 mmol, Aldrich) of 4-nitrophenol and 1.2 g (8.0 mmol, Schweizerhall) of 1-hydroxybenzotriazole monohydrate. The mixture was cooled to 0° and treated with 1.6 mL (14 mmol, Aldrich) of 4-methylmorpholine, followed by the addition of 1.5 g (8.0 mmol, Bathem) of WSC. The mixture was stirred at 0° for 3 hrs and at r.t. for 90 hrs. The crude reaction mixture was concentrated in high vacuum. The residue was diluted with 300 mL of EtOAc, washed with 300 mL of 1N HCl and 300 mL of a saturated aqueous solution of NaHCO₃ and brine; dried (MgSO₄) and concentrated in vacuo The residue was dissolved in 200 mL of EtOAc and washed with 200 mL of 1N NaOH and brine; dried (MgSO₄) and concentrated in vacuo to afford 3.16 g (5.1 mmol, 73%) of title compound as a foam.

G. (2R-trans)-1-[N,N-Bis[(1,1-dimethylethoxy)carbonyl]-5-hydroxy-L-norvalyl]-4-methy-2-piperidinecarboxylic acid, ethyl ester A clear solution of 3.16 g (5.1 mmol) of Part F compound in 100 mL of methanol (Baker) was cooled to −20° and treated with 1.9 g (51 mmol, Aldrich) of sodium borohydride, portionwise, over a period of 15 min keeping the temperature below −20°. The yellow mixture was allowed to stir at −30° for 30 min. The yellow reaction mixture was allowed to warm to r.t., after 10 min, an exotherm ensued and the temperature increased over 25°. The recovered crude mixture was partitioned between 200 mL of EtOAc and 200 mL of 1N HCl. The organic layer was washed with 200 mL of a saturated aqueous solution of NaHCO₃ and brine; dried (MgSO₄) and concentrated in vacuo. The crude product was purified by flash chromatography (100 g, Merck silica gel, 50% EtOAc/hexane) to afford 1.6 g (3.3 mmol, 65%) of title compound as a light yellow oil.

H. (2R-trans)-1-[N,N-Bis[(1,1-dimethylethoxy)carbonyl]-5-[(methylsulfonyl)oxy]-L- norvalyl]-4-methyl-2-piperidinecarboxylic acid, ethyl ester The clear solution of 1.5 g (3.0 mmol) of Part G compound in 6 mL of CH₂Cl₂ (distilled from P₂O₅) was cooled to −30° and treated with 640 μL (4.6 mmol) of triethylamine (EtoN) (distilled from CaH₂), followed by the addition of 284 μL (4.6 mmol, Aldrich) of methanesulfonyl chloride. The mixture was stirred at −30° for 1.5 hrs. The crude mixture was washed with mL of 1N HCl and 6 mL of a saturated aqueous solution of NaHCO₃ and brine; dried (MgSO₄), and concentrated in vacuo to afford 1.73 g (3.1 mmol, 100%) of title compound as a light yellow oil.

I. (2R-trans)-1-[N,N-Bis[(1,1-dimethylethoxy)carbonyl]-5-azido-L-norvalyl]-4- methyl-2-piperidinecarboxylic acid, ethyl ester The light yellow solution of 1.7 g (3.0 mmol) of Part H compound in 7 mL of DMF (Burdick and Jackson) was treated with 548 mg (8.4 mmol, Aldrich) of sodium azide at r.t. for 43 hrs. The crude reaction mixture was filtered. The filtrate was concentrated in high vacuum. The residue was diluted in 200 mL of Et₂O and washed with a 5% aqueous solution of sodium thiosulfate, and brine; dried (Na₂SO₄) and concentrated in vacuo to afford 1.41 g (2.8 mmol, 92%) of title compound as an oil.

J. (2R-trans)-1-[N²,N²-Bis[(1,1-dimethylethoxy)carbonyl]-L-ornithyl]-4-methyl-2-piperidinecarboxylic acid, ethyl ester To a clear solution of 1.35 g (2.6 mmol) of Part I compound in 7 mL of methanol (Baker) was added 174 mg of 10% palladium on activated carbon (Aldrich). The mixture was stirred under an atmosphere of hydrogen (balloon) for 16 hrs. The crude mixture was filtered through a (Millipore, type FH 0.5 μm) polycarbonate membrane. The filtrate was concentrated in vacuo to afford 1.27 g (2.6 mmol, 100%) of title compound as an oil.

K. (2R-trans)-1-[N²,N²-Bis[(1,1-dimethylethoxy)carbonyl]-N⁵-(1-oxo-2-pyridinyl) -L-ornithyl]-4-methyl-2-piperidinecarboxylic acid, ethyl ester A clear solution of 1.20 g (2.5 mmol) of Part J compound in 9 mL of n-butanol (Mallinckrodt) was treated with 2.1 g (12 mmol, Aldrich) of 2-chloropyridine N-oxide hydrochloride followed by the addition of 1.56 g (18.6 mmol, Mallinckrodt) of sodium bicarbonate. The slurry was stirred at 100° for 21 hrs. The crude reaction mixture was cooled then filtered. The filtrate was concentrated in vacuo. The residue was diluted in 200 mL of EtOAc; washed with brine; dried (MgSO₄) and concentrated in vacuo. The crude product was purified by flash chromatography (100 g, Merck silica gel, 20% EtOAc/MeOH) to afford 426 mg (0.74 mmol, 30%) of title compound as a foam.

L. (2R-trans)-1-[N²,N²-Bis[(1,1-dimethylethoxy)carbonyl]-N⁵-(2-pyridinyl)-L-ornithyl]-4-methyl-2-piperidinecarboxylic acid, ethyl ester A yellow solution of 425 mg (0.73 mmol) of Part K compound in 15 mL of absolute EtOH (Pharmco) was treated with 232 mg (3.7 mmol, Aldrich) of ammonium formate and 425 mg of 10% palladium on activated carbon (Aldrich). The reaction mixture was refluxed for 1.5 hrs. The crude mixture was filtered through a (Millipore, type FH 0.5 μm) polycarbonate membrane. The filtrate was concentrated in vacuo. The crude product was purified by flash chromatography (15 g, Merck silica gel, 50% EtOAc/hexane) to afford 150 mg (0.27 mmol, 36%) of title compound as a foam.

M. (2R-trans)-1-[N$^5$-(2-Pyridinyl)-L-ornithyl]-4-methyl-2-piperidinecarboxylic acid, ethyl ester, dihydrochloride A clear solution of 150 mg (0.27 mmol) of Part compound in 2 mL of 1,4-dioxane (Burdick and Jackson) was treated with 700 μL (4M in dioxane, 2.8 mmol, Aldrich) of HCl solution at r.t. for 16 hrs. The mixture was concentrated in vacuo to give 124 mg (0.28 mmol, 100%) of title compound as a foam.

N. (2R-trans)-1-[N$^2$-[(7-Methoxy-2-naphthalenyl)sulfonyl]-N$^5$-(2-pyridinyl)-L-ornithyl]-4-methyl-2-piperidinecarboxylic acid ethyl ester A white slurry of 120 mg (0.28 mmol) of Part M compound in 2 mL of CH$_2$Cl$_2$ (distilled from P$_2$O$_5$) was cooled to 0° and treated with 154 μL (1.1 mmol) of Et$_3$N (distilled from CaH$_2$) followed by the dropwise addition of a solution of 78 mg (0.30 mmol) of Example 7, Part D sulfonyl chloride in 2 mL of CH$_2$Cl$_2$, keeping the temperature below 5°. The reaction mixture was stirred at 0° for 3 hrs. The mixture was concentrated in vacuo. The residue was triturated in EtOAc. The Et$_3$N.HCl salt was removed by suction filtration. The filtrate was washed with 20 mL of 1N HCl and 20 mL of a saturated aqueous solution of NaHCO$_3$ and brine; dried (MgSO$_4$) and concentrated in vacuo. The crude product was purified by flash chromatography (25 g, Merck silica gel, 100% EtOAc) to afford 113 mg (0.19 mmol, 71%) of title compound as a white solid.

O. (2R-trans)-1-[N$^2$-[(7-Methoxy-2-naphthalenyl)sulfonyl)-N$^5$-(2-pyridinyl)-L-ornithyl]-4-methyl-2-piperidinecarboxylic acid The clear solution of 100 mg (0.17 mmol) of Part N compound in 3 mL of 2:1 THF/H$_2$O was treated with 15 mg (0.36 mmol) of lithium hydroxide monohydrate at room temperature for 64 hrs. The mixture was treated with 0.36 ml (0.36 mmol) of 1N HCl. The crude reaction mixture was concentrated in vacuo. The residue was partitioned between 50 mL of EtOAc and 30 mL of H$_2$O. The organic layer was washed with brine; dried (MgSO$_4$) and concentrated in vacuo The crude product was purified by flash chromatography (25 g, Merck silica gel, 15% MeOH/CH$_2$Cl$_2$) to afford 81 mg (0.15 mmol, 85%) of title compound as a white solid, m.p. soft 165° C.-decomposed 265° C.

Analysis calcd. for C$_{28}$H$_{34}$N$_4$O$_6$S.0.48CH$_2$Cl$_2$.2.3-H$_2$O: C,53.82; H,6.25; N,8.81; S,5.04; Cl,5.35

Found: C,53.71; H,5.66; N,8.54; S,4.69; Cl,5.20.

EXAMPLE 12

(S)-7-Methoxy-N-[1-[(4-methyl-1-piperidinyl)carbonyl]-4-(3-pyridazinylamino)butyl]-2-naphthalene-sulfonamide A. (S)-2-[Bis[(1,1-dimethylethoxy)carbonyl]amino]-5-[(6-chloro-3-pyridazinyl)amino]-1-(4-methyl-1-piperidinyl)-1-pentanone A clear solution of 1.9 g (4.6 mmol) of Example 5 G amine in 13 mL of n-butanol was treated with 1.36 g (9.20 mmol,Aldrich) of 3,6-dichloropyridazine followed by the addition of 1.54 g (18.3 mmol,Mallinckrodt) of sodium bicarbonate. The mixture was stirred at 100° C. for 21 hrs. The crude reaction mixture was concentrated in vacuo. The residue was diluted in 200 mL of EtOAc; washed with 200 mL of a saturated aqueous solution of NaHCO$_3$ and brine; dried (MgSO$_4$) and concentrated in vacuo. The resulting crude product was purified by flash chromatography (60 g, Merck silica gel, 50% EtOAc/hexane) to afford 933 mg (1.77 mmol, 39%) of title compound as a yellow foam.

B. (S)-2-[Bis[(1,1-dimethylethoxy)carbonyl]amino]-1-(4-methyl-1-piperidinyl)-5-(3-pyridazinylamino)-1-pentanone To a yellow solution of 930 mg (177 mmol) of Part A compound in 30 mL of MeOH (Burdick and Jackson) was added 930 mg (Aldrich) of palladium hydroxide on activated carbon. The mixture was stirred under an atmosphere of hydrogen (balloon) at r.t. for 4 hrs. The crude reaction mixture was filtered through a (Millipore, type FH 0.5 μm) polycarbonate; membrane. The filtrate was concentrated in vacuo. The dark oil residue was diluted in 15 mL of EtOAc; washed with a saturated aqueous solution of NaHCO$_3$, and brine; dried (MgSO$_4$) and concentrated in vacuo. The dark brown crude product was purified by flash chromatography (13 g, Merck silica gel, 100% EtOAc) to afford 474 mg (9.64 mmol, 54%) of title compound as a white solid.

C. (S)-2-Amino-1-(4-methyl-1-piperidinyl)-5-(3-pyridazinylamino)-1-pentanone, dihydrochloride A clear solution of 474 mg (0.96 mmol) of Part B compound in 2 mL of 1,4-dioxane (Burdick and Jackson) was treated with 2.4 mL (4M in dioxane, 9.7 mmol, Aldrich) of HCl solution at r.t. for 4 hrs. The crude reaction mixture was concentrated in vacuo to afford 390 mg (0.96 mmol, 100%) of title compound as a white foam.

D. (S)-7-Methoxy-N-[1-[(4-methyl-1-piperidinyl)carbonyl]-4-(3-pyridazinylamino) butyl]-2-naphthalenesulfonamide A clear slurry of 130 mg (0.36 mmol) of Part C compound in 2.5 mL of CH$_2$Cl$_2$ (distilled from P$_2$O$_5$) was cooled to 0° C. and treated with 199 μL (1.43 mmol) of Et$_3$N (distilled from CaH$_2$) followed by the dropwise addition of a solution of 101 mg (3.9 mmol) of Example 7, Part D sulfonyl chloride in 2.5 mL of CH$_2$Cl$_2$, keeping the temperature below 0° C. The reaction mixture was stirred at 0° C. for 3 hrs. The crude reaction mixture was concentrated in vacuo. The residue was dissolved in EtOAc and filtered. The filtrate was washed with brine; dried (MgSO$_4$) and concentrated in vacuo. The crude product was purified by flash chromatography (50 g, 60 Merck silica gel, 100% EtOAc then 1/9:(1/9:NH$_4$OH/MeOH)/CH$_2$Cl$_2$) to afford 90 mg (0.18 mmol, 49%) of title compound as an off-white foam.

Analysis calcd. for C$_{26}$H$_{33}$N$_5$O$_4$S: C, 61.04; H,6.50; N,13.69; S,6.27.

Found: C, 60.87; H,6.40; N,13.46; S,6.66

Following the procedures described in Examples 1 to 12 and in the specification, the following compounds in accordance with the present invention (Formula I) were prepared.

| | Melting Point °C. (where available) Optical Rotation and Chemical Analysis |
|---|---|
| 13. (S)-3,4-Dihydro-2,2,5,7,8-pentamethyl-N-[1-[(4-methyl-1-piperidinyl)carbonyl]-4-(2-pyridinylamino)butyl]-2H-1-benzopyran-6-sulfonamide | Opt. rot.: $[\alpha]_D = +60°$ (c = 0.50 in MeOH) |
| Elemental Analysis (%) | |
| Calc'd: C, 64.72; H, 7.97; N, 10.06; S, 5.76 | |
| Found: C, 64.63; H, 7.89; N, 9.97; S, 5.98 | |
| 14. (S)-6-Methoxy-N-[1-[(4- | Opt. rot.: |

-continued

| | Melting Point °C. (where available) Optical Rotation and Chemical Analysis |
|---|---|
| methyl-1-piperidinyl)carbonyl]-4-(2-pyridinylamino)butyl]-2-naphthalenesulfonamide | $[\alpha]_D = +73°$ (c = 0.50 in MeOH) |
| Elemental Analysis (%) | |
| Calc'd: C, 63.51; H, 6.71; N, 10.97; S, 6.28 | |
| Found: C, 63.25; H, 6.79; N, 10.63; S, 6.16 | |
| 15. (S)-5-Ethoxy-N-[1-[(4-methyl-1-piperidinyl)carbonyl]-4-(2-pyridinylamino)butyl]-1-naphthalenesulfonamide | Opt. rot.: $[\alpha]_D = +58°$ (c = 0.50 in MeOH) |
| Elemental Analysis (%) | |
| Calc'd: C, 64,10; H, 6.92; N, 10.68; S, 6.11 | |
| Found: C, 64.01; H, 7.11; N, 10.25; S, 5.84 | |
| 16. (S)-7-Ethoxy-N-[1-[(4-methyl-1-piperidinyl)carbonyl]-4-(2-pyridinylamino)butyl]-2-naphthalenesulfonamide | Opt. rot.: $[\alpha]_D = +18°$ (c = 0.42 in MeOH) |
| Elemental Analysis (%) | |
| Calc'd: C, 64.10; H, 6.92; N, 10.68; S, 6.11 | |
| Found: C, 63.91; H, 6.94; N, 10.48; S, 5.92 | |
| 17. (S)-N-[1-[(4-methyl-1-piperidinyl)carbonyl]-4-(3-pyridazinylamino)butyl]-2-naphthalenesulfonamide | Opt. rot.: $[\alpha]_D = +46°$ (c = 0.50 in MeOH) |
| Elemental Analysis (%) | |
| Calc'd: C, 62.35; H, 6.49; N, 14.54; S, 6.66 | |
| Found: C, 62.26; H, 6.43; N, 14.29; S, 6.63 | |
| 18. (S)-5-(Dimethylamino)-N-[1-[(4-methyl-1-piperidinyl)carbonyl]-4-(3-pyridazinylamino)butyl]-1-naphthalenesulfonamide | Opt. rot.: $[\alpha]_D = +61°$ (c = 0.42 in MeOH) |
| Elemental Analysis (%) | |
| Calc'd: C, 61.81; H, 6.92; N, 16.02; S, 6.11 | |
| Found: C, 61.66; H, 6.98; N, 15.78; S, 6.08 | |

Other compounds of the invention which may be prepared following the procedures set out in the specification and working Examples are set out below.

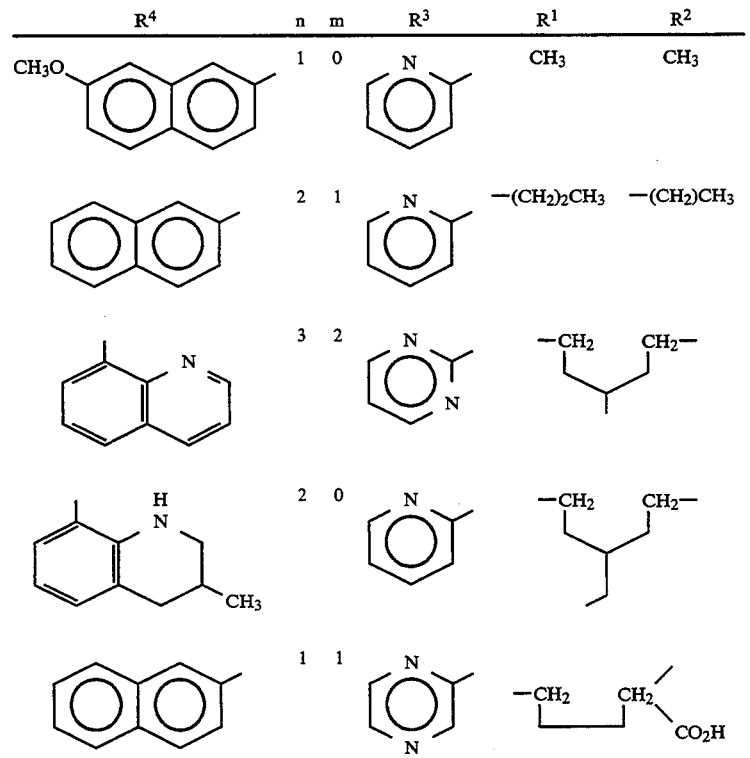

-continued

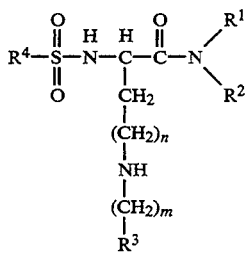

| R⁴ | n | m | R³ | R¹ | R² |
|---|---|---|---|---|---|
| 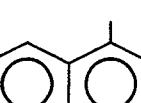 OCH₃ | 3 | 0 | 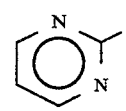 | —CH₂ | 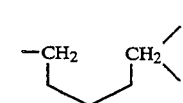 CO₂H |
| 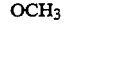 OC₂H₅ | 2 | 0 |  | —CH₂ | CH₂—  O |

What is claimed is:

1. A compound of the structure

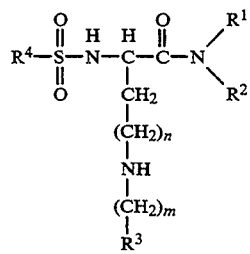

including all stereoisomers thereof, wherein n is 1, 2 or 3;

m is 0, 1 or 2;

R¹ and R² may be the same or different and are independently hydrogen, lower alkyl, cycloalkyl, aryl, heteroaryl, or heteroarylalkyl, or R¹ and R² may be taken together with the nitrogen atom to which they are attached to form a 4- to 8-membered N-containing heterocyclic ring which may be unsubstituted or substituted on a carbon atom with lower alkyl, carboxy, carboalkoxy, aryl or cycloalkyl, or any of lower alkyl, aryl or cycloalkyl linked through an O, S or N atom to the heterocyclic ring;

R³ is monocyclic heteroaryl; and

R⁴ is aryl, alkyl, cycloalkyl, heteroaryl, quinolinyl, or tetrahydroquinolinyl, and pharmaceutically acceptable salts thereof.

2. The compound as defined in claim 1 having the structure

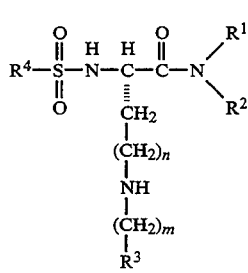

3. The compound as defined in claim 1 wherein R⁴ is aryl.

4. The compound as defined in claim 2 wherein R⁴ is 2-naphthyl.

5. The compound as defined in claim 1 wherein R¹ and R² are taken together with the N-atom to which they are attached to form a 4- to 8-membered heterocyclic.

6. The compound as defined in claim 4 wherein R¹ and R² are taken together with the N-atom to which they are attached to form

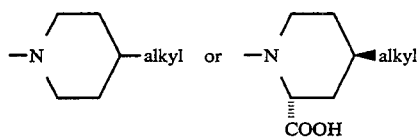

7. The compound as defined in claim 6 wherein alkyl is CH₃.

8. The compound as defined in claim 1 wherein R³ is

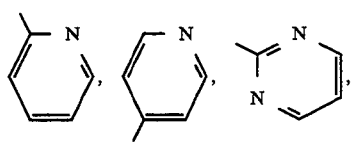

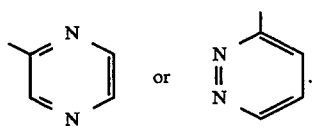

9. The compound as defined in claim 1 wherein n is 2 and m is 0.

10. The compound as defined in claim 1 wherein $R^1$, and $R^2$ are taken together with the N-atom to which they are attached to form

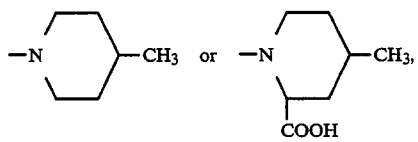

n is 2, m is 0, $R^3$ is

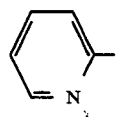

and $R^4$ is

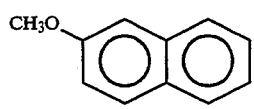

11. The compound as defined in claim 1 having the structure

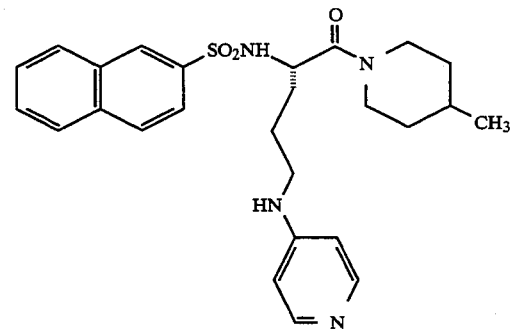

or

12. The compound as defined in claim 1 having the structure

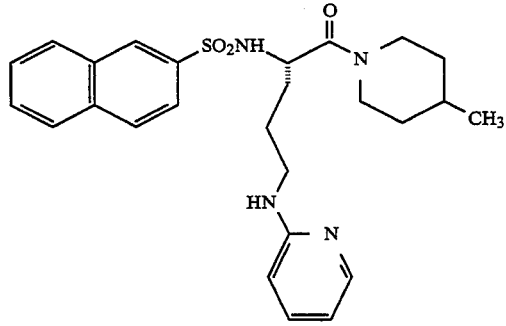

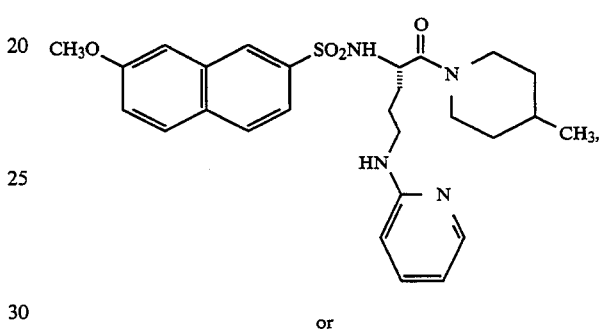

or

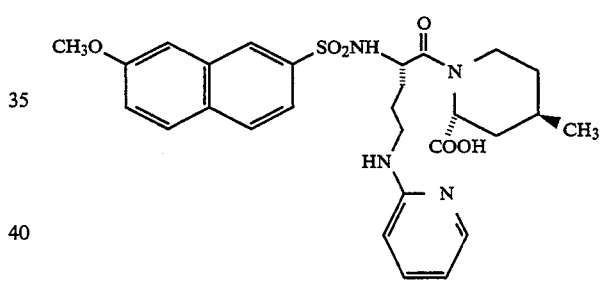

13. The compound as defined in claim 1 which is (S)-N-[1-[(4-methyl-1-piperidinyl)carbonyl]-4-(4-pyridinylamino )butyl]-2-naphthalenesulfonamide, (S)-N-[1-[(4-methyl-1-piperidinyl)carbonyl]-4(2-pyridinylamino)butyl]-2-naphthalenesulfonamide, (S)-N-[1-[(4-methyl-1-piperidinyl)carbonyl]-3(2-pyridinylamino)propyl]-2-naphthalenesulfonamide, (S)-N-[1-[(4-methyl-1-piperidinyl)carbonyl]-5(2-pyridinylamino)pentyl]-2-naphthalenesulfonamide, (S)-N-[1-[(4-methyl-1-piperidinyl)carbonyl]-4(2-pyrimidinylamino)butyl]-2-naphthalenesulfonamide, (S)-N-[1-[(4-methyl-1-piperidinyl)carbonyl]-4( 2-pyrazinylamino)butyl]-2-naphthalenesulfonamide, (S)-3-methyl-N-[1-[(4-methyl-1-piperidinyl)carbonyl]-4-(2-pyridinylamino)butyl]-8-quinolinesufonamide, (S)-3,4-dihydro-2,2,5,7,8-pentamethyl-N-[1-[(4-methyl-1-piperidinyl)carbonyl]-4-(2-pyridinylamino)-butyl]-2H-1-benzopyran-6-sulfonamide, (S)-6-methoxy-N-[1-[(4-methyl-1-piperidinyl)carbonyl]-4-(2-pyridinylamino)butyl]-2-naphthalene sulfonamide, (S)-5-ethoxy-N-[1-[(4-methyl-1-piperidinyl)carbonyl]-4-(2-pyridinylamino)butyl]-1-naphthalenesulfonamide, (S)-7-ethoxy-N-[1-[(4-methyl-1-piperidinyl)carbonyl]-4-(2-pyridinylamino)butyl]-2-naphthalenesulfonamide, (S)-7-methoxy-N-[1-[(4-methyl-1-piperidinyl)carbonyl]-4-(3-pyridazinylamino)butyl]-2-naphthalenesulfonamide, (S)-N-[1-[(4-methyl-1-piperidinyl)carbonyl]-4-(3-pyridazinylamino)butyl]-2-naphthalenesulfonamide, (S)-5-(dimethylamino)-N-[1-[(4-methyl-1-piperidinyl)carbonyl]-4-(3-pyridazinylamino)butyl]-1-naphthalenesulfonamide, or a pharmaceutically acceptable salt of any of the above.

14. The compound as defined in claim 1 which is (S)-7-methoxy-N-[1-[(4-methyl-1-piperidinyl)carbonyl]-4-(2-pyridinylamino)butyl]-2-naphthalenesulfonamide, (S)-5-(dimethylamino)-N-[1-[(4-methyl-1-piperidinyl)-carbonyl-4-(2-pyridinylamino)butyl]-1-naphthalenesulfonamide, 1,2,3,4-tetrahydro-3-methyl-N-[(S)-1-[(4-methyl-1-piperidinyl)carbonyl]-4-(2-pyridinylamino)butyl]-8-naphthalenesulfonamide, 2:1 mixture of 3-methyl isomers, (2R-trans)-1-[N2-[(7-methoxy-2-naphthalenyl)sulfonyl]-N5-(2-pyridinyl)-L-ornithyl]-4-methyl-2-piperidinecarboxylic acid or a pharmaceutically acceptable salt of any of the above.

15. A method of inhibiting or preventing formation of blood clots, which comprises administering to a patient in need of treatment a therapeutically effective amount of a compound as defined in claim 1.

16. A pharmaceutical composition comprising a compound as defined in claim 1 and a pharmaceutically acceptable carrier therefor.

17. A compound of the structure

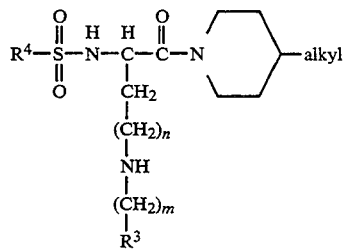

including all stereoisomers thereof, wherein n is 1, 2 or 3;

m is 0, 1 or 2;

$R^3$ is heteroaryl; and $R^4$ is aryl, alkyl, cycloalkyl, heteroaryl, quinolinyl, or tetrahydroquinolinyl, and pharmaceutically acceptable salts thereof; wherein the term "heteroaryl" refers to

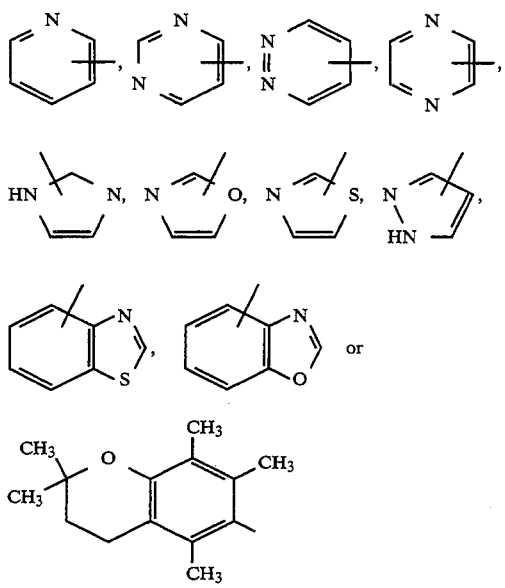

and any of the above which may optionally include 1 or 2 substituents selected from the group consisting of halogen, lower alkyl, lower alkoxy, carboxy, amino, lower alkylamino and dilower alkylamino.

* * * * *

UNITED STATES PATENT AND TRADEMARK OFFICE
CERTIFICATE OF CORRECTION

PATENT NO. : 5,371,091
DATED : December 6, 1994
INVENTOR(S) : Raj N. Misra et al It is certified that error appears in the above-identified patent and that said Letters Patent is hereby corrected as shown below:

Column 35,
Claim 14, line 32, please change "8-naphthalenesulfonamide" to --8-quinolinesulfonamide--.

Signed and Sealed this

Twentieth Day of June, 1995

Attest:

BRUCE LEHMAN

Attesting Officer    Commissioner of Patents and Trademarks